US011026891B2

(12) United States Patent
Leroux et al.

(10) Patent No.: US 11,026,891 B2
(45) Date of Patent: Jun. 8, 2021

(54) TRANSMEMBRANE PH-GRADIENT POLYMERSOMES AND THEIR USE IN THE SCAVENGING OF AMMONIA AND ITS METHYLATED ANALOGS

(71) Applicant: ETH Zurich, Zurich (CH)

(72) Inventors: Jean-Christophe Leroux, Zurich (CH); Simon Matoori, Zurich (CH); Aaron Christoph Schmidt, Zurich (CH)

(73) Assignee: Eth Zurich, Zurich (CH)

( * ) Notice: Subject to any disclaimer, the term of this patent is extended or adjusted under 35 U.S.C. 154(b) by 0 days.

(21) Appl. No.: 16/326,133

(22) PCT Filed: Aug. 15, 2017

(86) PCT No.: PCT/IB2017/054966
§ 371 (c)(1),
(2) Date: Feb. 15, 2019

(87) PCT Pub. No.: WO2018/033856
PCT Pub. Date: Feb. 22, 2018

(65) Prior Publication Data
US 2019/0183800 A1    Jun. 20, 2019

(30) Foreign Application Priority Data
Dec. 13, 2016 (EP) .................................. 16203817

(51) Int. Cl.
*A61K 9/127* (2006.01)
*A61K 9/00* (2006.01)
(Continued)

(52) U.S. Cl.
CPC .......... *A61K 9/1273* (2013.01); *A61K 9/0053* (2013.01); *A61K 31/194* (2013.01);
(Continued)

(58) Field of Classification Search
None
See application file for complete search history.

(56) References Cited

U.S. PATENT DOCUMENTS

| 6,835,394 B1 | 12/2004 | Discher |
| 2005/0003016 A1 | 1/2005 | Discher |

(Continued)

FOREIGN PATENT DOCUMENTS

| CN | 104771382 | 7/2015 |
| EP | 2695606 | 2/2014 |

(Continued)

OTHER PUBLICATIONS

Bajaj et al. 190 AST-120 (Spherical Carbon Adsorbent) in Covert Hepatic Encephalopathy: Results of the Astute Trial J. Hepatol 2013; 58:S84.

(Continued)

*Primary Examiner* — Sin J Lee

(74) *Attorney, Agent, or Firm* — Faegre Drinker Biddle & Reath LLP

(57) ABSTRACT

The present invention provides polymersomes comprising non-biodegradable amphiphilic block-copolymers and their enteral (e.g., oral) or topical use in the treatment of an ammonia or ammonia methylated analog-associated disease or disorder or symptom thereof (e.g., hyperammonemia or trimethylaminuria). More particularly, it provides a polymersome comprising (a) a membrane, which comprises a block copolymer of poly(styrene) (PS) and poly(ethylene oxide) (PEO), wherein the PS/PEO molecular weight ratio is higher than 1.0 and lower than 4.0; and (b) a core which encloses an acid. It also provides a method of making the polymersome comprising mixing the copolymer-containing organic solvent phase with an aqueous phase containing the acid.

19 Claims, 13 Drawing Sheets

(51) Int. Cl.
| | |
|---|---|
| A61K 47/32 | (2006.01) |
| A61K 47/34 | (2017.01) |
| A61K 31/194 | (2006.01) |
| A61P 9/00 | (2006.01) |
| A61P 5/00 | (2006.01) |
| A61P 43/00 | (2006.01) |
| A61P 3/00 | (2006.01) |
| A61P 25/00 | (2006.01) |
| A61P 13/12 | (2006.01) |
| A61P 13/02 | (2006.01) |

(52) U.S. Cl.
CPC .............. *A61K 47/32* (2013.01); *A61K 47/34* (2013.01); *A61P 3/00* (2018.01); *A61P 5/00* (2018.01); *A61P 9/00* (2018.01); *A61P 13/02* (2018.01); *A61P 13/12* (2018.01); *A61P 25/00* (2018.01); *A61P 43/00* (2018.01)

(56) References Cited

U.S. PATENT DOCUMENTS

| | | | |
|---|---|---|---|
| 2005/0019265 | A1 | 1/2005 | Hammer |
| 2009/0214419 | A1* | 8/2009 | Therien ................ A61K 9/1273 514/1.1 |
| 2010/0098773 | A1 | 4/2010 | Hammer |
| 2011/0256225 | A1 | 10/2011 | Ghoroghchian |
| 2014/0248606 | A1* | 9/2014 | Beller .................. C12Q 1/6806 435/5 |
| 2015/0216802 | A1* | 8/2015 | Leroux ................ A61M 1/287 424/450 |

FOREIGN PATENT DOCUMENTS

| | | |
|---|---|---|
| WO | WO200132146 | 5/2001 |
| WO | WO2006096571 | 9/2006 |
| WO | WO2007133807 | 11/2007 |
| WO | WO2009117188 | 9/2009 |
| WO | WO2010017177 | 2/2010 |
| WO | WO2010148395 | 12/2010 |
| WO | WO2010148653 | 12/2010 |
| WO | WO2012007567 | 1/2012 |
| WO | WO2012094679 | 7/2012 |
| WO | WO2012140415 | 10/2012 |
| WO | WO2013025801 | 2/2013 |
| WO | WO2014130761 | 8/2014 |
| WO | WO2015031911 | 3/2015 |
| WO | WO2015050869 | 4/2015 |
| WO | WO2015059180 | 4/2015 |

OTHER PUBLICATIONS

Blankenstein T et al. (2015). Point-of-care (POC) diagnosis of bacterial vaginosis (BV) using VGTest™ ion mobility spectrometry (IMS) in a routine ambulatory care gynecology clinic. Archives of gynecology and obstetrics 292(2), 355-362.
Bosoi et al. AST-120 (spherical carbon adsorbent) lowers ammonia levels and attenuates brain edema in bile duct-igated rats. Hepatology 2011; 53:1995-2002.
Cashman Jr et al. (1999) In-vitro and in-vivo studies inhibition of human flavin-containing monooxygenase form 3 (FMO3) in the presence of dietary indoles. Biochem Pharmacol 58, 1047-1055.
Cashman Jr et al. (2003). Biochemical and clinical aspects of the human flavin-containing monooxygenase form 3 (FMO3) related to trimethylaminuria. Current drug metabolism, 4(2), 151-170.
CN104771382 Zhang Jul. 15, 2015 English translation.
Danks DM et al. (1976) Trimethylaminuria: diet does not always control the fishy odor. The New England Journal of Medicine, 295(17), 962-962.
Davankov and Tsyurupa Structure and properties of hypercrosslinked polystyrene—the first representative of a new class of polymer networks Reactive Polymers 1990;13:27-42.
Discher et al. Emerging applications of polymersomes in delivery: From molecular dynamics to shrinkage of tumors Progress in Polymer Science 2007, 32(8-9), pp. 838-857.
Ernenweim et al. Self-Assembling Amphiphilic Hyperbranched Polyglycerol—Polystyrene Copolymers for Encapsulation Macromolecular Chemistry and Physics 2015 216(16): 1729-1736.
Forster et al. Liposome-supported peritoneal dialysis in the treatment of severe hyperammonemia: An investigation on potential interactions J Control Release. May 28, 2018;278:57-65.
Hayward et al. Dewetting Instability during the Formation of Polymersomes from Block-Copolymer-Stabilized Double Emulsions Langmuir 2006, 22(10): 4457-4461.
Hocine et al. Polymersomes with PEG corona: structural changes and controlled release induced by temperature variation. Langmuir. Feb. 5, 2013;29(5):1356-69.
Leevy et al. Hospitalizations during the use of rifaximin versus lactulose for the treatment of hepatic encephalopathy. Dig Dis Sci 2007; 52:737-41.
Levy J. The effects of antibiotic use on gastrointestinal function. The American Journal of Gastroenterology, 2000, 95(1), S8-S10.
Matoori and Leroux Recent advances in the treatment of hyperammonemia.ADDR 2015; 90:55-68.
Men et al. Methods for production of uniform small-sized polymersome with rigid membrane Polymer Chemistry 2016, 7(24):3941-4128.
Mullen et al. Rifaximin is safe and well tolerated for long-term maintenance of remission from overt hepatic encephalopathy Clin Gastroenterol Hepatol 2014;12:1390-1397.e2.
Neff et al. Update on the management of cirrhosis—focus on cost-effective preventative strategies Clinicoecon Outcomes Res. 2013; 5: 143-152.
Neuvonen and Elonen Effect of activated charcoal on absorption and elimination of phenobarbitone, carbamazepine and phenylbutazone in man Eur J Clin Pharmacol 1980; 17:51-57.
Neuvonen and Olkkola Oral activated charcoal in the treatment of intoxications. Role of single and repeated doses Med Tocixol 1988; 3:33-58.
Poordad Review article: the burden of hepatic encephalopathy. Aliment Pharmacol Ther. 2007; 25: 3-9.
Rose Ammonia-Lowering Strategies for the Treatment of Hepatic Encephalopathy Clinical Pharmacology & Therapeutics 2012; 92:321-331.
Schulman et al. A multicenter, randomized, double-blind, placebo-controlled, dose-ranging study of AST-120 (Kremezin) in patients with moderate to severe CKD Am J Kidney Dis 2006; 47:565-577.
Song et al. Preparation of Surfactant-Resistant Polymersomes with Ultrathick Membranes through RAFT Dispersion Polymerization. ACS Appl Mater Interfaces. 2016, 8(27):17033-7.
Stepanova et al. In-hospital mortality and economic burden associated with hepatic encephalopathy in the United States from 2005 to 2009Clin Gastroenterol Hepatol 2012; 10:1034-1041.e1.
Szoka and Papahadjopoulos. Procedure for preparation of liposomes with large internal aqueous space and high capture by reverse-phase evaporation PNAS 1978; 75:4194-4198.
Tang WW et al. (2013). Intestinal microbial metabolism of phosphatidylcholine and cardiovascular risk. New England Journal of Medicine 368(17), 1575-1584.
Tang WW et al. (2015). Gut microbiota-dependent trimethylamine N-oxide (TMAO) pathway contributes to both development of renal insufficiency and mortality risk in chronic kidney disease. Circulation research 116(3), 448-455.
Todd WA (1979). Psychosocial problems as the major complication of an adolescent with trimethylaminuria. The Journal of pediatrics, 94(6), 936-937.
Treacy E et al. (1995). Trimethylaminuria, fish odour syndrome: a new method of detection and response to treatment with metronidazole. Journal of inherited metabolic disease, 18(3), 306-312.
Van Dongen A Block Copolymer for Functionalisation of Polymersome Surfaces 2008, 29(40): 321-325.
Vilstrup et al. Hepatic encephalopathy in chronic liver disease: 2014 Practice Guideline by the American Association for the Study of Liver Diseases and the European Association for the Study of the Liver.Hepatology 2014; 60:715-735.

(56) References Cited

OTHER PUBLICATIONS

Wang Z et al. (2011). Gut flora metabolism of phosphatidylcholine promotes cardiovascular disease. Nature 472(7341), 57-63.
Wang Z et al. (2015). Non-lethal inhibition of gut microbial trimethylamine production for the treatment of atherosclerosis. Cell 163(7), 1585-1595.
Wilcken B (1993). Acid soaps in the fish odour syndrome. BMJ: British Medical Journal, 307(6917), 1497.
Wise PM et al. (2011). Individuals reporting idiopathic malodor production: demographics and incidence of trimethylaminuria. The American journal of medicine 124(11), 1058-1063.
Yamazaki H et al. (2004). Effects of the dietary supplements, activated charcoal and copper chlorophyllin, on urinary excretion of trimethylamine in Japanese trimethylaminuria patients. Life sciences, 74(22), 2739-2747.
Yeung CK et al. (2007). Functional characterization of genetic variants of human FMO3 associated with trimethylaminuria. Archives of biochemistry and biophysics, 464(2), 251-259.
Yuan et al. The "crew-cut" aggregates of polystyrene-b-poly(ethylene oxide)-b-polystyrene triblock copolymers in aqueous media European Polymer Journal 2003, 39(4):767-776.
Extended European Search Report issued in EP16184371.9, dated Jan. 26, 2017, 5 pages.
International Preliminary Report on Patentability issued in PCT/IB2017/054966, dated Feb. 28, 2019, 7 pages.
International Search Report and Written Opinion issued in PCT/IB2017/054966, dated Nov. 3, 2017, 13 pages.
International Search Report and Written Opinion issued in PCT/IB2018/056887, dated Dec. 19, 2018, 13 pages.

\* cited by examiner

TRANSMEMBRANE PH-GRADIENT POLYMERSOMES AND THEIR USE IN THE SCAVENGING OF AMMONIA AND ITS METHYLATED ANALOGS

CROSS-REFERENCE TO RELATED APPLICATIONS

This application is a National Entry Application of PCT application no. PCT/IB2017/054966, filed on Aug. 15, 2017 and published in English under PCT Article 21(2), which itself claims benefit of EP applications No. 16184371.9, filed on Aug. 16, 2016, No. 16200067.3, filed on Nov. 22, 2016 and EP16203817.8, filed on Dec. 13, 2016. All documents above are incorporated herein in their entireties by reference.

FIELD OF THE INVENTION

The present invention relates to transmembrane pH-gradient polymersomes and their use in the scavenging of ammonia and its methylated analogs (e.g., trimethylamine (TMA)). More specifically, the present invention is concerned with polymersomes comprising non-biodegradable amphiphilic block-copolymers and their enteral (e.g., oral) or topical use in the scavenging of ammonia and/or its methylated analogs (e.g., TMA) for the treatment of e.g., hyperammonemia, trimethylaminuria, cardiovascular and/or chronic kidney diseases.

BACKGROUND OF THE INVENTION

Ammonia ($NH_3$) and its methylated analogs (e.g., TMA ($N(CH_3)_3$) possess similar physicochemical properties (e.g., low molecular weight, similar pKa and log P, etc.). They are both mainly produced in the gastrointestinal tract and their presence in excess in the body is associated with various disorders and symptoms thereof.

Ammonia

Ammonia ($NH_3$) is a neurotoxic endogenous metabolite which accumulates in patients suffering from impaired liver function (e.g., due to liver cirrhosis, acute liver failure, portosystemic shunting, inborn errors of ammonia metabolism) (Matoori and Leroux ADDR 2015; 90:55-68).

High ammonia levels in the blood (hyperammonemia) are associated with hepatic encephalopathy, a neuropsychiatric condition with serious acute and chronic manifestations potentially leading to death (Vilstrup et al. Hepatology 2014; 60:715-735). Hepatic encephalopathy led to >20 000 hospitalizations in 2009 and costs of >7b USD in the USA alone (Stepanova et al., Clin Gastroenterol Hepatol 2012; 10:1034-1041.e1; Poordad, Alim Pharmacol Therap 2006; 25:3-9). In-hospital cost per single hospitalization due to hepatic encephalopathy increased from 22'511 USD in 2004 to 37'398 USD in 2010 (Neff et al. Clinicoecon Outcomes Res. 2013; 5: 143-152).

One of the main sources of ammonia in the body are urease-producing bacteria in the colon (Matoori and Leroux supra). Therefore, the clinical practice guidelines for hepatic encephalopathy recommend as first- and second-line therapy for hepatic encephalopathy the non-absorbable disaccharide lactulose (a commonly used laxative) and the antibiotic rifaximin (e.g., Xifaxan™) which tackle the generation and absorption of colonic ammonia in a rather unspecific manner (Vilstrup et al. supra). Both of these orally available therapies fail to control the symptoms and progression of hepatic encephalopathy in a large fraction of the patient population and many patients under these therapies suffer from adverse reactions such as diarrhea (Vilstrup et al. supra; Rose Clinical Pharmacology & Therapeutics 2012; 92:321-331; Leevy et al., Dig Dis Sci 2007; Mullen et al. Clin Gastroenterol Hepatol 2014; 12: 1390-1397.e2).

Orally administered spherical carbon adsorbent (AST-120, Kremezin®) were also disclosed for sequestering ammonia and improving hyperammonemia-associated symptoms in an animal model of hepatic encephalopathy (Bosoi et al. Hepatology 2011; 53:1995-2002). Mechanistically, ammonia adsorbs to AST-120 microparticles in the gut and is subsequently excreted via the feces. In a clinical trial with hepatic encephalopathy patients, AST-120 treatment did not lead to clinical improvement in neuropsychological symptoms, probably due to the insufficient binding of ammonia (Bajaj et al. J. Hepatol 2013; 58: S84, Bosoi et al. supra). Carbon adsorbents are known to bind to a variety of compounds and bear the risk of interfering with important endogenous or exogenous substances (Schulman et al. Am J Kidney Dis 2006; 47:565-577; Neuvonen and Elonen Eur J Clin Pharmacol 1980; 17:51-57; Neuvonen and Olkkola Med Toxicol 1988; 3:33-58).

Due to the chronic nature of hepatic encephalopathy, ammonia-removing treatment strategies based on extracorporeal approaches (e.g., hemodialysis) are not ideal because they are invasive and mainly suited to treat severe acute hyperammonemic episodes.

An ideal treatment for patients suffering from hyperammonemia-induced hepatic encephalopathy would be an enteral treatment (e.g., oral), potent and selective in ammonia uptake, and stable in the harsh environment of the gastrointestinal tract.

Trimethylamine

Trimethylamine (TMA) ($N(CH_3)_3$) is a tertiary amine which is generated in the intestine by the bacterial metabolism of dietary substances (e.g., choline, carnitine, lecithin) (Wang Z et al. (2011). Nature 472(7341), 57-63; Wise P M et al. (2011). The American journal of medicine 124(11), 1058-1063). TMA is subsequently oxidized by flavin monooxygenase 3 into the non-odorous trimethylamine-N-oxide (TMAO) in the liver (Yeung C K et al. (2007). Archives of biochemistry and biophysics, 464(2), 251-259). TMA and its metabolite TMAO are involved in the etiology of several diseases.

Trimethylaminuria (also known as fish odor syndrome) is an autosomal recessive disorder linked to flavin monooxygenase 3 deficiency (Yeung et al., supra). Patients suffering from trimethylaminuria generally present with malodor (often associated with rotten fish) due to elevated amounts of TMA in bodily fluids (urine, sweat) and expired air (Wise et al., supra). The diagnosis of trimethylaminuria is usually based on a dietary choline challenge and subsequent urine analysis of TMA and TMAO (Wise et al., supra). The perceptible smell mainly stems from the skin surface and varies depending on the diet (Wise et al., supra). Due to their malodor, trimethylaminuria patients often suffer from psychological symptoms (e.g., depression, suicidal tendencies) and social isolation (Todd W A (1979). The Journal of pediatrics, 94(6), 936-937).

Enhanced TMAO levels were also associated with an increased risk of cardiovascular disease and chronic kidney disease (Tang W W et al. (2013). New England Journal of Medicine 368(17), 1575-1584; Tang W W et al. (2015). Circulation research 116(3), 448-455); and the inhibition of gut microbial TMA production led to a reduction in atherosclerotic lesions (Wang Z et al. (2015). Cell 163(7), 1585-1595).

Furthermore, TMA was found to be a contributor to the unpleasant smell in bacterial vaginosis (Blankenstein T et al. (2015). Archives of gynecology and obstetrics 292(2), 355-362).

Trimethylaminuria Treatments. In the treatment of trimethylaminuria, dietary restrictions such as avoiding *Brassica* vegetables and carnitine-, choline-, or lecithin-rich foods are recommended to decrease the malodor (Cashman J R et al. (1999) In-vitro and in-vivo studies inhibition of human flavin-containing monooxygenase form 3 (FMO3) in the presence of dietary indoles. Biochem Pharmacol 58, 1047-1055; Cashman J R et al. (2003). Biochemical and clinical aspects of the human flavin-containing monooxygenase form 3 (FMO3) related to trimethylaminuria. Current drug metabolism, 4(2), 151-170; Danks D M et al. (1976) Trimethylaminuria: diet does not always control the fishy odor. The New England Journal of Medicine, 295(17), 962-962). However, these restrictive measures are cumbersome for the patients and do not always result in a sufficient decrease in malodorous body vapors (Danks et al., supra). Certain orally applied antibiotics (e.g., neomycin, metronidazole), which inhibit the growth and metabolism of TMA-generating microbes in the intestine, may alleviate the symptoms temporarily (Danks et al., supra; Treacy E et al. (1995). Journal of inherited metabolic disease, 18(3), 306-312). However, a beneficial effect was not observed in all patients (Treacy et al., supra) and long-term antibiotic use bears the risk of gastrointestinal adverse reactions (Levy J (2000). The American Journal of Gastroenterology, 95(1), S8-S10). Scavenging TMA by adsorption on orally administered activated charcoal has also been shown to be beneficial in certain patients suffering from trimethylaminuria (Yamazaki H et al. (2004). Effects of the dietary supplements, activated charcoal and copper chlorophyllin, on urinary excretion of trimethylamine in Japanese trimethylaminuria patients. Life sciences, 74(22), 2739-2747). Furthermore, the use of acidic soap is recommended as TMA is less volatile in the protonated state (Wilcken B (1993). Acid soaps in the fish odor syndrome. BMJ: British Medical Journal, 307(6917), 1497).

The ammonia methylated analog dimethylamine (DMA) shares similar physicochemical properties as TMA and ammonia and is produced in the GI tract. It is a precursor of a known carcinogen.

The present description refers to a number of documents, the content of which is herein incorporated by reference in their entirety.

SUMMARY OF THE INVENTION

This invention describes the composition, preparation and use of transmembrane pH-gradient polymersomes for ammonia and its methylated analogs (e.g., TMA) detoxification/scavenging via the enteral (e.g., oral) route and the topical route. As shown herein, the polymersomes of the present invention strongly sequester ammonia and its methylated analogs (e.g., TMA) in simulated gastrointestinal fluids and resist to this harsh environment. Furthermore, the polymersomes of the present invention strongly sequester TMA in emulsions (e.g., topical formulations such as lotions and creams).

More particularly, the polymersomes of the present invention were shown to exhibit their sequestering properties when diluted in a medium mimicking the conditions encountered in the intestine, contrarily to transmembrane pH-gradient liposomes for instance (see e.g., Example 1). The stability and efficacy of the polymersomes in the gastrointestinal environment was demonstrated in Examples below by showing the uptake of ammonia under variable simulated gastrointestinal conditions (high bile salt concentrations (Examples 6-8 and 13), hypo- and hyperosmolarity (Examples 9), presence of digestive enzymes (Example 10) and high cation concentrations (Example 11)). The stability and efficacy of the polymersomes were also demonstrated in oil in water (o/w) emulsions corresponding to e.g., a topical formulation (Example 13).

This invention describes for example polymersomes composed of non-biodegradable amphiphilic block-copolymers (e.g. poly(styrene)-b-poly(ethylene oxide) (PS-b-PEO, also known as poly(styrene)-b-poly(ethylene glycol), PS-b-PEG)).

More specifically, in accordance with an aspect of the present invention, there is provided a polymersome, (a) the membrane of which comprises a block copolymer of a hydrophobic uncharged non-biodegradable polymer and a hydrophilic uncharged non-biodegradable polymer as defined herein, wherein the hydrophobic uncharged non-biodegradable polymer/hydrophilic uncharged and non-biodegradable polymer molecular weight ratio is higher than 1.0 and lower than 4.0 (e.g., higher than 1.0 and lower than 3.0); and (b) the core of which encloses an acid.

More specifically, in accordance with an aspect of the present invention, there is provided a polymersome comprising (a) a membrane, which comprises a block copolymer of a hydrophobic uncharged non-biodegradable polymer and a hydrophilic uncharged non-biodegradable polymer as defined herein, wherein the hydrophobic uncharged non-biodegradable polymer/hydrophilic uncharged and non-biodegradable polymer molecular weight ratio is higher than 1.0 and lower than 4.0 (e.g., higher than 1.0 and lower than 3.0); and (b) a core which encloses an acid.

More specifically, in accordance with an aspect of the present invention, there is provided a polymersome consisting of (a) a membrane, which comprises a block copolymer of a hydrophobic uncharged non-biodegradable polymer and a hydrophilic uncharged non-biodegradable polymer as defined herein, wherein the hydrophobic uncharged non-biodegradable polymer/hydrophilic uncharged and non-biodegradable polymer molecular weight ratio is higher than 1.0 and lower than 4.0 (e.g., higher than 1.0 and lower than 3.0); and (b) a core which encloses an acid.

In accordance with a more specific aspect of the present invention, there is provided a polymersome, (a) the membrane of which comprises a block copolymer of poly(styrene) (PS) and poly(ethylene oxide) (PEO), wherein the PS/PEO molecular weight ratio is higher than 1.0 and lower than 4.0 (e.g., higher than 1.0 and lower than 3.0); and (b) the core of which encloses an acid. In accordance with a more specific aspect of the present invention, there is provided a polymersome comprising (a) a membrane, which comprises a block copolymer of poly(styrene) (PS) and poly(ethylene oxide) (PEO), wherein the PS/PEO molecular weight ratio is higher than 1.0 and lower than 4.0 (e.g., higher than 1.0 and lower than 3.0); and (b) the core of which encloses an acid. In accordance with a more specific aspect of the present invention, there is provided a polymersome consisting of (a) a membrane, which comprises a block copolymer of poly(styrene) (PS) and poly(ethylene oxide) (PEO), wherein the PS/PEO molecular weight ratio is higher than 1.0 and lower than 4.0 (e.g., higher than 1.0 and lower than 3.0); and (b) the core of which encloses an acid. The polymersomes of the present invention may be cross-linked or not.

In a specific embodiment, there is provided a polymersome, (a) the membrane of which consists of a block copolymer of poly(styrene) (PS) and poly(ethylene oxide) (PEO), wherein the PS/PEO molecular weight ratio is higher than 1.0 and lower than 4.0 (e.g., higher than 1.0 and lower than 3.0); and (b) the core of which encloses an acid. In a specific embodiment, there is provided a polymersome comprising (a) a membrane, which consists of a block copolymer of poly(styrene) (PS) and poly(ethylene oxide) (PEO), wherein the PS/PEO molecular weight ratio is higher than 1.0 and lower than 4.0 (e.g., higher than 1.0 and lower than 3.0); and (b) a core which encloses an acid. In a specific embodiment, there is provided a polymersome consisting of (a) a membrane, which consists of a block copolymer of poly(styrene) (PS) and poly(ethylene oxide) (PEO), wherein the PS/PEO molecular weight ratio is higher than 1.0 and lower than 4.0 (e.g., higher than 1.0 and lower than 3.0); and (b) a core which encloses an acid.

In a specific embodiment of the polymersome of the present invention, the block copolymer is a diblock copolymer. In another specific embodiment of the polymersome of the present invention, the acid is in a concentration that produces a pH between 1 and 6, preferably between 2 and 5, more preferably between 2 and 4, when the polymersome is hydrated. In another specific embodiment of the polymersome of the present invention, the acid is within an aqueous acidic solution. In another specific embodiment of the polymersome of the present invention, the pH within the aqueous acidic solution is between 1 and 6, preferably between 2 and 5, more preferably between 2 and 4. In another specific embodiment of the polymersome of the present invention, the acid is (i) a hydroxy acid such as citric acid, isocitric acid, malic acid, tartaric acid or lactic acid; (ii) a small chain fatty acid such as acetic acid; (iii) a sugar acid such as uronic acid; (iv) a dicarboxylic add such as malonic add; (v) a tricarboxylic acid such as propane-1,2,3-tricarboxylic add or aconitic acid; (vi) a tetracarboxylic acid such as 1,2,3,4-butanetetracarboxylic acid; (vii) a pentacarboxylic add such as 1,2,3,4,5-pentanepentacarboxylic acid; (viii) a polymeric poly(carboxylic acid) such as poly(acrylic acid) or poly(methacrylic acid); (ix) a polyaminocarboxylic acid such as ethylenediaminetetraacetic acid; or (x) a combination of at least two thereof. In a more specific embodiment, it is a hydroxy add, and preferably citric add. In another specific embodiment, the polymersome of the present invention is prepared by a method comprising mixing an organic solvent containing the copolymer with an aqueous phase containing the acid. In another specific embodiment of the polymersome of the present invention, the organic solvent is water immiscible or partially water miscible. In another specific embodiment of the polymersome of the present invention, the polymersome core further encloses ammonia. In another specific embodiment of the polymersome of the present invention, the polymersome core further encloses ammonia or its methylated analog, the methylated analog being preferably TMA. In another specific embodiment of the polymersome of the present invention, the polymersome core further encloses an ammonia methylated analog (e.g., TMA).

In accordance with another aspect of the present invention, there is provided a composition comprising the polymersome of the present invention, and at least one pharmaceutically acceptable excipient.

In another specific embodiment of the composition of the present invention, the composition is in liquid, or solid form. In another specific embodiment of the composition of the present invention, the composition is in liquid, semi solid or solid form.

In accordance with another aspect of the present invention, there is provided the polymersome of the present invention or the composition of the present invention, for enteral use. In accordance with another aspect of the present invention, there is provided the polymersome of the present invention or the composition of the present invention, for enteral use or topical use.

In accordance with another aspect of the present invention, there is provided the polymersome of the present invention or the composition of the present invention, for topical use.

In accordance with another aspect, the polymersome of the present invention or the composition of the present invention is for use in scavenging ammonia.

In accordance with another aspect, the polymersome of the present invention or the composition of the present invention is for use in scavenging an ammonia methylated analog (e.g., TMA).

The polymersome or composition of the present invention, for use in the treatment of an ammonia or ammonia methylated analog-associated disease or disorder, or a symptom thereof, and preferably hyperammonemia or trimethylaminuria.

In accordance with another aspect, the polymersome of the present invention or the composition of the present invention is for use in the treatment of hyperammonemia.

In accordance with another aspect, the polymersome of the present invention or the composition of the present invention is for use in the treatment of trimethylaminuria or a symptom thereof or a TMA-associated cardiovascular disease or a symptom thereof or a TMA-associated kidney disease or a symptom thereof or TMA-associated bacterial vaginosis or a symptom thereof, in a subject in need thereof.

In a specific embodiment of the polymersome for use, the trimethylaminuria symptom and/or bacterial vaginosis symptom is malodor (from e.g., skin and/or urine and/or expired air and/or vagina).

In another aspect, there is provided a method of using the polymersome of the invention or the composition of the invention comprising (e.g., enterally or topically) administering the polymersome or composition to a subject in need thereof. In another aspect, there is provided a use of the polymersome of the invention or the composition of the invention for (e.g., enteral or topical) administration to a subject in need thereof. In another aspect, there is provided a use of the polymersome of the invention or the composition of the invention as a medicament.

In accordance with another aspect, the above method(s) or use(s) is for (of for the manufacture of a medicament for) scavenging ammonia, in accordance with another aspect, the above method(s) or use(s) is for (of for the manufacture of a medicament for) scavenging an ammonia methylated analog (e.g., TMA) in a subject in need thereof. In accordance with another aspect, the above method(s) or use(s) is for (of for the manufacture of a medicament for) the treatment of an ammonia or ammonia methylated analog-associated disease or disorder, or a symptom thereof, and preferably hyperammonemia or trimethylaminuria, more preferably hyperammonemia, in a subject in need thereof. In accordance with another aspect, the above method(s) or use(s) is for (of for the manufacture of a medicament for) the treatment of trimethylaminuria or a symptom thereof or a TMA-associated cardiovascular disease or a symptom thereof or a TMA-associated kidney disease or a symptom thereof or TMA-associated bacterial vaginosis or a symptom thereof, in a subject in need thereof. In a specific embodiment of the above method(s) or use(s), the trimethylaminuria symptom and/or bacterial vaginosis symptom is malodor (from e.g., skin and/or urine and/or expired air and/or vagina).

In accordance with yet another aspect of the present invention, there is provided a method of making the polymersome of the present invention, comprising: (a) dissolving the block copolymer of PS and PEO in an organic solvent, preferably a water-immiscible or partially water-miscible organic solvent, to form a copolymer-containing organic phase; (b) mixing the copolymer-containing organic solvent phase with an aqueous phase containing the acid so as to form the polymersome; and (c) removing the organic solvent.

In a specific embodiment of the method of the present invention, the aqueous phase comprises between 50 and 700 mM of acid.

In another aspect, the present invention provides a kit comprising the above-mentioned polymersomes or compositions and instructions to use the polymersomes or compositions for scavenging ammonia in a subject in need thereof.

In another aspect, the present invention provides a kit comprising the above-mentioned polymersomes or compositions and instructions to use the polymersomes or compositions for treating hyperammonemia in a subject in need thereof.

In another aspect, the present invention provides a kit comprising the above-mentioned polymersomes or compositions and instructions to use the polymersomes or compositions for scavenging an ammonia methylated analog (e.g., TMA).

In another aspect, the present invention provides a kit comprising the above-mentioned polymersomes or compositions and instructions to use the polymersomes or compositions for treating trimethylaminuria or a symptom thereof or a TMA-associated cardiovascular disease or a symptom thereof or a TMA-associated kidney disease or a symptom thereof or TMA-associated bacterial vaginosis or a symptom thereof, in a subject in need thereof.

In a specific embodiment of the kit, the trimethylaminuria symptom and/or bacterial vaginosis symptom is malodor (from e.g., skin and/or urine and/or expired air and/or vagina).

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
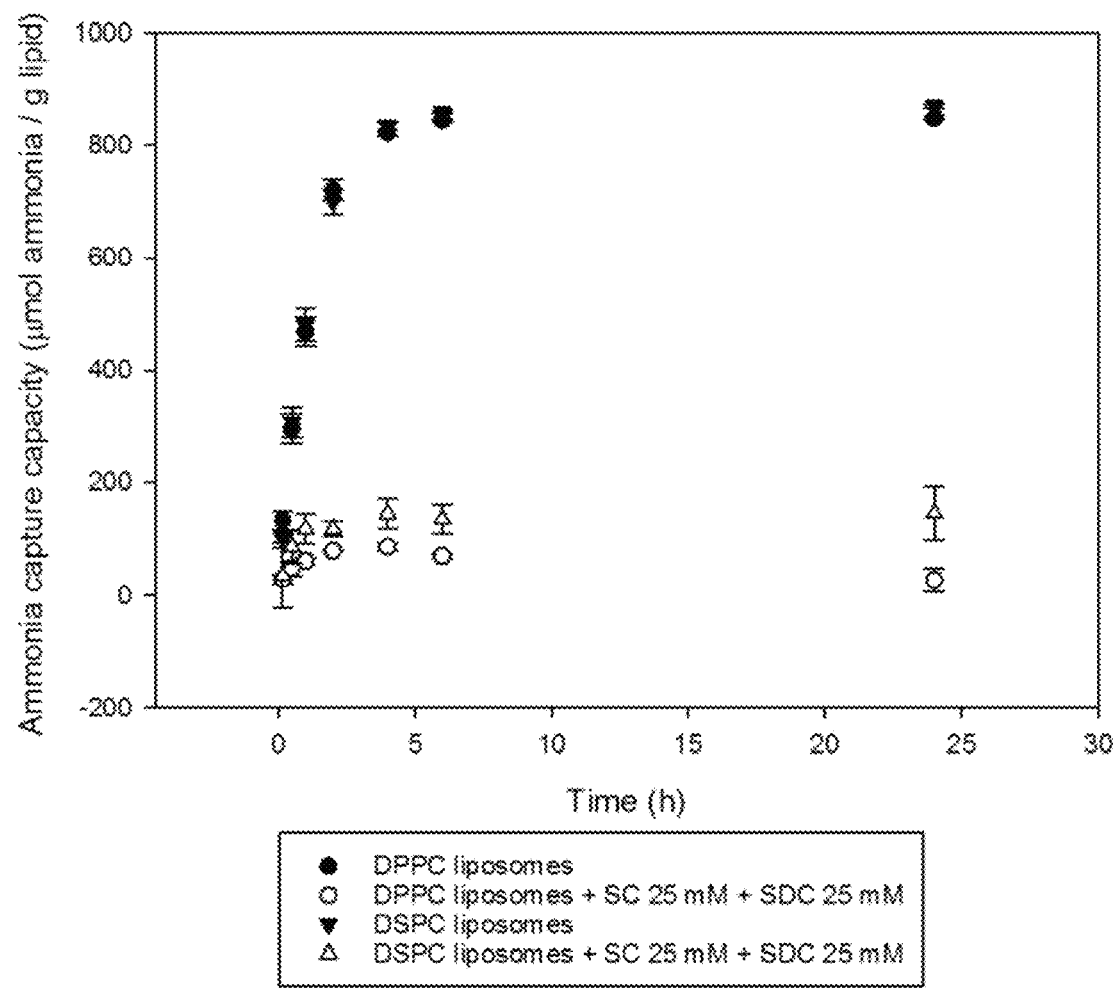
FIG. 1 is a graph showing the in vitro ammonia uptake of transmembrane pH-gradient liposomes that were prepared using a film hydration method (n=3, mean and standard deviation).

The present invention encompasses polymersomes possessing transmembrane pH-gradient to capture ammonia and/or its methylated analogs (e.g., TMA), compositions comprising the polymersomes, processes for making the polymersomes and the use of these polymersomes and compositions.

Polymersomes

Polymersomes are vesicles, the bilayer membrane of which is assembled from synthetic copolymers. They have mean diameters ranging from 50 nm to 100 µm or more, in a specific embodiment, ranging from 100 nm to 40 µm, as determined by laser diffraction. Although tested polymersomes of the present invention having mean diameters varying between 100 nm to 40 µm were able to effectively encapsulate ammonia, there is no reason to believe that polymersomes with a diameter larger than 40 µm could not also be effective.

Polymersomes of the present invention comprise non-biodegradable amphiphilic block copolymers and are prepared using an organic solvent.

The mechanism of action of the present invention is based on the pH gradient across the polymersome membrane. The acidic agent contained in the aqueous polymersome core possesses a pH different (lower than) from the physiological pH in the intestine and the skin. Hence, ammonia and its methylated analogs (e.g., TMA) can diffuse through the hydrophobic polymeric membrane of the polymersomes in their uncharged state and be then trapped in their protonated (ionized) state (e.g., ammonium in the case of ammonia) in the inner compartment. While ammonia and TMA are mainly existing in their protonated state at the pH of the intestine and skin, there is always a small fraction in its non-ionized state. This fraction can diffuse in the polymersomes and be trapped in their protonated state inside the polymersomes, which in turn displaces the equilibrium, bringing more ammonia and TMA inside the vesicles.

As used herein the property «transmembrane pH gradient to capture ammonia» and/or «transmembrane pH gradient to capture ammonia and/or its methylated analogs» therefore refers to the ability of the polymersomes of the present invention to sequester ammonia (and/or its methylated analogs) when diluted in a medium mimicking the conditions encountered in the intestine or on the skin.

As used herein, the terms "ammonia methylated analogs" refers, without being so limited, to TMA, and DMA. In a specific embodiment, it refers to TMA.

Block Copolymers

"Polymers" are macromolecules comprising connected monomeric units. The monomeric units may be of a single type (homogeneous), or a variety of types (heterogeneous). When two or more different monomers unite together to polymerize, their result is called a copolymer. A copolymer made of a sequence of two or more monomers of a single type (a block) covalently joined to two or more monomers of another type (another block) is called a block copolymer. A copolymer made of two block types covalently joined together is called a diblock, of three block types, is called a triblock, etc. Block copolymers can comprise, as a result of the specific synthesis used to generate them, different end groups.

Polymersomes of the present invention comprise block copolymers. In a specific embodiment, the block copolymers of the present invention are diblock or triblock copolymers. These block copolymers are amphiphilic and are formed of at least two polymers, namely an aromatic highly hydrophobic polymer (e.g. poly(styrene)) and a hydrophilic uncharged and non-biodegradable polymer. In a more specific embodiment, the block copolymer is a diblock copolymer (e.g., poly(styrene)-b-poly(ethylene oxide) (PS-b-PEO)), or a triblock copolymer (e.g., PEO-b-PS-b-PEO)) (i.e. PS PEO block copolymers)).

An "amphiphilic" copolymer is one containing both hydrophilic (water-soluble) and hydrophobic (water-insoluble) groups.

As used herein the term "non-biodegradable" means non-hydrolysable in gastrointestinal conditions (e.g., resistant to degradation by enzymes (e.g., protease, lipase) or degradation through other means (e.g., pH) in the gastrointestinal tract).

Hydrophobic Uncharged Non-Biodegradable Polymer

In a specific embodiment, the hydrophobic uncharged non-biodegradable polymer used in copolymers of the present invention is a poly(ethylethylene) (—($CH_2$—CH($C_2H_5$))$_n$—, i.e. —($C_4H_8$)$_n$—) or a poly(styrene) (—($CH_2$—CH(Ph))$_n$—, i.e. —($CH_2$—CH($C_6H_5$))$_n$—, i.e. —($C_8H_8$)$_n$—). In specific embodiments, the hydrophobic uncharged non-biodegradable polymer is a poly(styrene). Poly(styrenes) for use in the present invention may include non-substituted and/or substituted/functionalized styrene monomers. Unless specifically defined otherwise, the term "poly(styrene)" is therefore used herein generically to designate a poly(styrene) that comprises exclusively non-substituted styrene monomers, a mix of substituted and non-substituted monomers or exclusively substituted monomers. The one or more substituents on the styrene monomer may include substituents on the phenyl and/or on the carbon on which the phenyl is attached and/or may form polycyclic derivatives with the phenyl (e.g., bicycles, tricycles, etc. comprising C3-C6 aryl(s) and/or C3-C6 cycloalkyl(s)). Potential substituents include alkyl (C1 to C7 (C1, C2, C3, C4, C5, C6 or C7, more specifically C1, C2 or C3), aryl (C3-C6), C3-C8 cycloalkyl, aryl-alkyl, acetoxyl, alkoxyl (methoxyl, ethoxyl, propanoxyl, butoxyl, etc.), halogen (Br, Cl, F, etc.), amine, amide, alkylamine, $NO_2$. The substituents may themselves be substituted. Without being so limited, the substituted styrene monomer include acetoxystyrene, benshydrylstyrene, benzyloxy-methoxystyrene, bromostyrene (2-, 3-, 4- or alpha), chlorostyrene (2-, 3-, 4- or alpha), fluorostyrene (2-, 3-, 4- or alpha), tert-butoxystyrene, tert-butylstyrene, chloro-methylstyrene, diclhlorostyrene, diflurostyrene, dimethoxystyrene, dimethylstyrene, dimethylvinylbenzylamine, diphenyl methyl pentene, (diphenylphosphino)styrene, ethoxystyrene, isopropenylaniline, isopropenyl-α,α-dimethylbenzyl isocyanate, [N-(methylaminoethyl)aminomethyl]styrene, methylstyrene, nitrostyrene, pentafluorophenyl 4-vinylbenzoate, pentafluorstyrne, (trifluormethyl)styrene (2-, 3-, or 4-), trimethylstyrene, vinylaniline (3-, or 4-), vinylanisole, vinylbenzoic acid (3-, 4-), vinylbenzyl chloride, (vinylbenzyl)trimethylammonium vinylbiphenyl, 4-vinylbenzocyclobutene (4-, etc.), vinylanthracene (9-, etc.), 2-vinylnaphthalene, vinyl-biphenyl (3-, 4-, etc.), etc. In particular embodiments, the substituted styrene monomer is an alkylstyrene (e.g., methyl styrene) or a tert-butylstyrene. In an embodiment, the PS comprises at least one substituted styrene monomer. The substituents may be non-ionic groups (e.g., methyl- or tert-butyl groups). In another specific embodiment, the styrene monomers in the poly(styrene) are unsubstituted.

Hydrophilic Uncharged Non-Biodegradable Polymer

Hydrophilic uncharged and non-biodegradable polymer that can be used with poly(styrene) in the block copolymer of the present invention include poly(ethylene oxide), poly (N-vinylpyrrolidone), poly(ethyl oxazoline), poly(methyl oxazoline), and polymers of oligoethylene glycol alkyl acrylate. In specific embodiments, the hydrophilic uncharged and non-biodegradable polymer is poly(ethylene oxide).

Poly(ethylene oxide) (PEO) for use in the present invention has the general formula: ($-$(O$-$CH$_2$$-$CH$_2$)$_n$$-$, i.e. $-$(C$_2$H$_4$O)$_n$$-$) and includes non-substituted and substituted/functionalized ethylene oxide monomers. Unless specifically defined otherwise, the term "poly(ethylene oxide)" or PEO is therefore used herein generically to designate a PEO that comprises exclusively non-substituted ethylene oxide monomers, a mix of substituted and non-substituted monomers or exclusively substituted monomers. In an embodiment, the PEO comprises at least one substituted ethylene oxide monomer. In another embodiment, the ethylene oxide monomers are unsubstituted.

Polymers' Proportion

The molecular weights of the PS and PEO blocks (e.g., diblock PS-b-PEO or triblock PEO-b-PS-b-PEO) can be varied as long as the structure and stability of the bilayer is preserved. The inventors found that stable PS PEO polymersomes form between a PS/PEO number average molecular weight ratio higher than 1.0 and lower than 4 (see e.g., Examples 6-13). In a specific embodiment, the ratio is about 1.1 or higher and lower than 4. In another specific embodiment, the ratio is about 1.2 or higher and lower than 4. In another specific embodiment, the ratio is about 1.3 or higher and lower than 4. In another specific embodiment, the ratio is about 1.4 or higher and lower than 4. In another specific embodiment, the ratio is higher than 1 and about 3.9 or lower. In a specific embodiment, the ratio is about 1.1 or higher and lower than 3.9. In another specific embodiment, the ratio is about 1.2 or higher and lower than 3.9. In another specific embodiment, the ratio is about 1.3 or higher and lower than 3.9. In another specific embodiment, the ratio is about 1.4 or higher and lower than 3.9. In another specific embodiment, the ratio is higher than 1 and about 3.8 or lower. In a specific embodiment, the ratio is about 1.1 or higher and lower than 3.8. In another specific embodiment, the ratio is about 1.2 or higher and lower than 3.8. In another specific embodiment, the ratio is about 1.3 or higher and lower than 3.8. In another specific embodiment, the ratio is about 1.4 or higher and lower than 3.8. In another specific embodiment, the ratio is higher than 1 and about 3.7 or lower. In a specific embodiment, the ratio is about 1.1 or higher and lower than 3.7. In another specific embodiment, the ratio is about 1.2 or higher and lower than 3.7. In another specific embodiment, the ratio is about 1.3 or higher and lower than 3.7. In another specific embodiment, the ratio is about 1.4 or higher and lower than 3.7. In another specific embodiment, the ratio is higher than 1 and about 3.6 or lower. In a specific embodiment, the ratio is about 1.1 or higher and lower than 3.6. In another specific embodiment, the ratio is about 1.2 or higher and lower than 3.6. In another specific embodiment, the ratio is about 1.3 or higher and lower than 3.6. In another specific embodiment, the ratio is about 1.4 or higher and lower than 3.6. In another specific embodiment, the ratio is higher than 1 and about 3.5 or lower. In a specific embodiment, the ratio is about 1.1 or higher and lower than 3.5. In another specific embodiment, the ratio is about 1.2 or higher and lower than 3.5. In another specific embodiment, the ratio is about 1.3 or higher and lower than 3.5. In another specific embodiment, the ratio is about 1.4 or higher and lower than 3.5. In another specific embodiment, the ratio is higher than 1 and about 3.4 or lower. In a specific embodiment, the ratio is about 1.1 or higher and lower than 3.4. In another specific embodiment, the ratio is about 1.2 or higher and lower than 3.4. In another specific embodiment, the ratio is about 1.3 or higher and lower than 3.4. In another specific embodiment, the ratio is about 1.4 or higher and lower than 3.4. In another specific embodiment, the ratio is higher than 1 and about 3.3 or lower. In a specific embodiment, the ratio is about 1.1 or higher and lower than 3.3. In another specific embodiment, the ratio is about 1.2 or higher and lower than 3.3. In another specific embodiment, the ratio is about 1.3 or higher and lower than 3.3. In another specific embodiment, the ratio is about 1.4 or higher and lower than 3.3. In another specific embodiment, the ratio is higher than 1 and about 3.2 or lower. In a specific embodiment, the ratio is about 1.1 or higher and lower than 3.2. In another specific embodiment, the ratio is about 1.2 or higher and lower than 3.2. In another specific embodiment, the ratio is about 1.3 or higher and lower than 3.2. In another specific embodiment, the ratio is about 1.4 or higher and lower than 3.2. In another specific embodiment, the ratio is higher than 1 and about 3.2 or lower. In a specific embodiment, the ratio is about 1.1 or higher and lower than 3.1. In another specific embodiment, the ratio is about 1.2 or higher and lower than 3.1. In another specific embodiment, the ratio is about 1.3 or higher and lower than 3.1. In another specific embodiment, the ratio is about 1.4 or higher and lower than 3.1. In a specific embodiment, the ratio is about 1.1 or higher and lower than 3. In another specific embodiment, the ratio is about 1.2 or higher and lower than 3. In another specific embodiment, the ratio is about 1.3 or higher and lower than 3. In another specific embodiment, the ratio is about 1.4 or higher and lower than 3. In another specific embodiment, the ratio is higher than 1 and about 2.9 or lower. In another specific embodiment, the ratio is about 1.1 or higher and about 2.9 or lower. In another specific embodiment, the ratio is about 1.2 or higher and about 2.9 or lower. In another specific embodiment, the ratio is about 1.3 or higher and about 2.9 or lower. In another specific embodiment, the ratio is about 1.4 or higher and about 2.9 or lower. In another specific embodiment, the ratio is higher than 1 and about 2.8 or lower. In another specific embodiment, the ratio is about 1.1 or higher and about 2.8 or lower. In another specific embodiment, the ratio is about 1.2 or higher and about 2.8 or lower. In another specific embodiment, the ratio is about 1.3 or higher and about 2.8 or lower. In another specific embodiment, the ratio is about 1.4 or higher and about 2.8 or lower. In another specific embodiment, the ratio is higher than 1 and about 2.7 or lower. In another specific embodiment, the ratio is higher than about 1.1 and about 2.7 or lower. In a specific embodiment, the ratio is between about 1.2 and about 2.7 or lower. In a specific embodiment, the ratio is about 1.3 or higher and about 2.7 or lower. In a specific embodiment, the ratio is about 1.4 or higher and about 2.7 or lower. In another specific embodiment, the ratio is higher than 1 and about 2.6 or lower. In another specific embodiment, the ratio is higher than about 1.1 and about 2.6 or lower. In a specific embodiment, the ratio is between about 1.2 and about 2.6 or lower. In a specific embodiment, the ratio is about 1.3 or higher and about 2.6 or lower. In a specific embodiment, the ratio is about 1.4 or higher and about 2.6 or lower. In another specific embodiment, the ratio is higher than 1 and about 2.5 or lower. In another specific embodiment, the ratio is higher than about 1.1 and about 2.5 or lower. In a specific embodiment, the ratio is between about 1.2 and about 2.5 or lower. In a specific embodiment, the ratio is about 1.3 or higher and about 2.5 or lower. In a specific embodiment, the ratio is about 1.4 or higher and about 2.5 or lower. In another specific embodiment, the ratio is higher than 1 and about 2.4 or lower. In another specific embodiment, the ratio is higher than about 1.1 and about 2.4 or lower. In a specific embodiment, the ratio is between about 1.2 and about 2.4 or lower. In a specific embodiment, the ratio is about 1.3 or higher and about 2.4 or lower. In a specific embodiment, the ratio is about 1.4 or higher and about 2.4 or lower. In another specific embodiment, the ratio is higher than 1 and about 2.3 or lower. In another specific embodiment, the ratio is higher than about 1.1 and about 2.3 or lower. In a specific embodiment, the ratio is between about 1.2 and about 2.3 or lower. In a specific embodiment, the ratio is about 1.3 or higher and about 2.3 or lower. In a specific embodiment, the ratio is about 1.4 or higher and about 2.3 or lower. In another specific embodiment, the ratio is higher than 1 and about 2.2 or lower. In another specific embodiment, the ratio is higher than about 1.1 and about 2.2 or lower. In a specific embodiment, the ratio is between about 1.2 and about 2.2 or lower. In a specific embodiment, the ratio is about 1.3 or higher and about 2.2 or lower. In a specific embodiment, the ratio is about 1.4 or higher and about 2.2 or lower. In another specific embodiment, the ratio is higher than 1 and about 2.1 or lower. In another specific embodiment, the ratio is higher than about 1.1 and about 2.1 or lower. In a specific embodiment, the ratio is between about 1.2 and about 2.1 or lower. In a specific embodiment, the ratio is about 1.3 or higher and about 2.1 or lower. In a specific embodiment, the ratio is about 1.4 or higher and about 2.1 or lower. In another specific embodiment, the ratio is higher than 1 and about 2.0 or lower. In another specific embodiment, the ratio is higher than about 1.1 and about 2.0 or lower. In a specific embodiment, the ratio is between about 1.2 and about 2.0 or lower. In a specific embodiment, the ratio is about 1.3 or higher and about 2.0 or lower. In a specific embodiment, the ratio is about 1.4 or higher and about 2.0 or lower.

Without limiting the generality of the above statements, PEOs having a molecular weight of between about 400 g/mol up to 20,000 g/mol are encompassed by the present invention. However, Applicants have no reason to expect that higher molecular weight PEO could not be effectively used in the present inventions. Polymers of smaller weight may be easier to manipulate. Typically, the PEO molecular weight is between 1000 and 5000 g/mol. The PS molecular weight is selected to satisfy the above described ratio. In accordance with the present invention, when the PEO has a molecular weight of about e.g., 20,000 g/mol, the PS molecular weight is lower than about 60,000 g/mol.

Properties of Polymersomes Made of Hydrophobic Uncharged Non-Biodegradable Polymer+Hydrophilic Uncharged Non-Biodegradable Polymer (Di- or Triblock Copolymers (e.g., PS-b-PEO or PEO-b-PS-b-PEO Copolymers))

Without being limited by this hypothesis, it is believed that the strong interaction of the highly hydrophobic polymer (e.g., aromatic (e.g., PS) with the capacity to make pi stacking interactions) in the vesicle membrane provides resistance against gastrointestinal fluids and excipients comprised in topical formulations such as oils and surfactants. Indeed, vesicles made of lipids (liposomes) or other amphiphilic diblock copolymers such as poly(butadiene)-b-poly(ethylene oxide) (PBD-b-PEO, also known as poly(butadiene)-b-poly(ethylene glycol), PBD-b-PEG; and poly(2-methyloxazoline)-b-poly(dimethylsiloxane)-b-poly(2-methyloxazoline), PMOXA-b-PDMS-b-PMOXA) are unable to take up ammonia in simple buffers (see e.g., Example 3), or are able to take up ammonia in simple buffers but lose their sequestering properties in media mimicking the intestinal fluids (see e.g., Examples 1 and 2).

Method of Preparation of Polymersomes

Preparation of Copolymer

Any known method for making copolymers can be used. Copolymers used in the Examples described herein were purchased from Advanced Polymer Materials Inc (PS-b-PEO and PMOXA-b-PDMS-b-PMOXA) and Polymer Source Inc (PBD-b-PEO).

Preparation of Polymersomes

The copolymer is dissolved in an organic solvent to form an organic phase, and the latter is mixed with the aqueous acidic solution (e.g., citric acid) (aqueous phase). Without being so limited, it is believed that the mixing allows a fine dispersion of the polymer in the water phase and the subsequent formation of stable polymersomes. The mixing step may be performed through different techniques. For instance, an oil in water (o/w) emulsion (i.e. polymer-containing organic solvent phase (i.e. oil phase) in acidic aqueous solution (i.e. water phase)), a reverse-phase evaporation, a nanoprecipitation, or a double emulsion method, may be used to mix the polymer-containing organic phase and the aqueous phase.

In the o/w emulsion method, the polymer-containing organic solvent is mixed with the aqueous acidic phase under sonication for a time and time sufficient to form an emulsion. In examples below, the aqueous phase was saturated with organic solvent under stirring for 30 minutes prior to the addition of the polymer-containing organic solvent phase. Subsequently, the polymer-containing organic solvent phase was added to the acid-containing aqueous phase under sonication for 3 minutes in an ice bath (to reduce the heat produced by the sonicator), using the following machine-specific parameters: amplitude 70, cycle 0.75 (UP200H, 200 W, 24 kHz, Hielscher Ultrasound Technology). Any method known in the art to create an emulsion may be used. The use of sonication as well as the specific sonication parameters and time appropriate for producing an emulsion will depend on the emulsion technique used. The emulsion does not need to be stable in the methods of preparation of the present invention.

In the reverse-phase evaporation method, a two-phase system comprising of a polymer-containing organic solvent and an acid-containing aqueous phase is sonicated, forming a water-in-oil (w/o) emulsion. The outer phase is evaporated under reduced pressure until a viscous gel-like state is formed. Polymersomes form upon the collapse of the gel state (Szoka and Papahadjopoulos. PNAS 1978; 75:4194-4198).

In the nanoprecipitation method, the polymers are dissolved in a suitable organic solvent, to which acid-containing water is slowly added.

In the double-emulsion method, polymersomes form in a w/o/w double emulsion containing an acid-containing aqueous inner phase, a polymer-containing completely or partially water immiscible organic solvent in the middle phase, and an aqueous outer phase.

The organic solvent is then removed from the polymersome using any known technique. The solvent is removed prior to administration to avoid detrimental solvent ingestion or skin exposure by the subject. Without being so limited an application of lower than ambient pressure, heat, filtration, cross-flow filtration, dialysis, or a combination of these methods may be used to remove the solvent.

After elimination of the organic solvent, the polymersomes can be used as is (with aqueous acid solution outside and inside the polymersomes), purified to change the composition of the non-encapsulated medium and/or further dried by conventional pharmaceutical drying procedures (e.g., freeze drying, spray drying). The drying step would allow the preparation of a solid dosage form (powder or capsules or tablet), which is easier to store and transport. When the polymersomes are meant to be orally administered, the dried polymersomes could then be dispersed again in an aqueous medium (e.g., water, juice) or taken as is by the patient (e.g., capsule, tablet). When the polymersomes are meant to be topically administered, the polymersomes can be dispersed in any relevant topical formulation such as an aqueous solution, gel, foam or an emulsion such as lotion or cream. In all such forms (as is, purified and/or dried), the polymersome core contains acid. This acid provides the transmembrane pH gradient to the polymersome when it is within the gastrointestinal tract or in the formulation on the skin. The so formed polymersomes of the present invention contain acid, potentially salt (i.e., partially deprotonated acid with counterion such as sodium, potassium or calcium) which may be added during the polymersome preparation to adjust the pH and/or osmolarity in the core, and, in their hydrated form, polymersomes further contain water.

When the polymersomes are hydrated (i.e. containing aqueous acidic core), the pH in their core is generally between about 1 and 6 (1, 1.5, 2, 2.5, 3, 3.5, 4, 4.5, 5, 5.5 or 6). In a specific embodiment, it is between about 1 and about 5, between about 1 and about 4.5, between about 1 and about 4, between about 1.5 and about 5, between about 1.5 and about 4.5, between about 1.5 and about 4, between about 2 and about 5, between about 2 and about 4.5, between about 2 and about 4, between about 2.5 and about 5, between about 2.5 and about 4.5, between about 2.5 and about 4, between about 3 and about 5, between about 3 and about 4.5, and between about 3 and about 5.

Although it is not necessary for the stability of the polymersomes of the present invention, they can also be crosslinked. For instance, a Friedel-Crafts reaction with the crosslinking agent p-xylylene-dichloride, 1,4-bis-chloromethyldiphenyl, monochlorodimethyl ether, dimethylformal, tris-(chloromethyl)-mesitylene, or p,p'-bis-chloromethyl-1,4-diphenylbutane may be used to crosslink poly(styrene) (Davankov and Tsyurupa, Reactive Polymers 1990; 13:27-42).

Solvent

The solvent used in the present invention dissolves the copolymer, and the polymer-containing solvent is then mixed with the acidic aqueous phase. During the mixing step (e.g., o/w emulsion), a fine dispersion of the polymer is formed in the aqueous phase. After the mixing step, the solvent is removed (e.g., evaporated) to ensure that the patients/subjects do not ingest it.

A concentration of about 2% to about 40% (v/v) solvent phase/aqueous phase ratio may be used. In a specific embodiment, the solvent phase/aqueous phase ratio is of about 5% to 30% (v/v). In another specific embodiment, the solvent phase/aqueous phase ratio is of about 5% to 20% (v/v). In another specific embodiment, the solvent phase/aqueous phase ratio is of about 5% to 15% (v/v). In another specific embodiment, the solvent phase/aqueous phase ratio is of about 10% (v/v). In a specific embodiment, the solvent phase/aqueous phase ratio in the resulting emulsion is about 9% (v/v).

In specific embodiments, the solvent is an organic solvent.

Without being so limited, the solvent may be a chlorinated solvent (e.g., dichloromethane see e.g., Ex. 5-6, 8-10, 12; or chloroform, see e.g., Ex. 7), arene or arene derivative (e.g., toluene, see e.g., Ex. 6), aliphatic solvent or aliphatic solvent derivative (e.g., hexane, 1-hexanol), ketone or ketone derivative (e.g., 2-hexanone), ether or ether derivative (e.g., diethylether), or mixtures thereof (e.g., when using an o/w emulsion, w/o/w double emulsion or reverse-phase evaporation technique).

In a specific embodiment, when an o/w emulsion is used to mix the polymer-containing organic phase and the aqueous phase, solvents useful for the present invention are water immiscible or partially water immiscible organic solvents. Without being so limited such solvents include e.g., dichloromethane see e.g., Ex. 5-6, 8-10, 12; or chloroform, see e.g., Ex. 7), arene or arene derivative (e.g., toluene, see e.g., Ex. 6), aliphatic solvent or aliphatic solvent derivative (e.g., hexane, 1-hexanol), ketone or ketone derivative (e.g., 2-hexanone), ether or ether derivative (e.g., diethylether), or mixtures thereof.

Acid and Acidic Solution

The acidic solution at the core of the polymersome preferably has a high buffering capacity at low pH for a high retention of basic compounds (e.g., ammonia, TMA, DMA). The acid is not toxic to animals, and does not (or only weakly) permeate out of the polymersome membrane.

Without being so limited, the acid enclosed in the polymersome core is (i) a hydroxy acid such as citric acid, isocitric acid, malic acid, tartaric acid, or lactic acid; (ii) a small chain fatty acid such as acetic acid; (iii) a sugar acid such as uronic acid; (iv) a dicarboxylic acid such as malonic acid; (v) a tricarboxylic acid such as propane-1,2,3-tricarboxylic acid or aconitic acid; (vi) a tetracarboxylic acid such as 1,2,3,4-butanetetracarboxylic acid; (vii) a pentacarboxylic acid such as 1,2,3,4,5-pentanepentacarboxylic acid; (viii) a polymeric poly(carboxylic acid) such as poly(acrylic acid) or poly(methacrylic acid); (ix) a polyaminocarboxylic acid such as ethylenediaminetetraacetic acid; or (x) a combination of at least two thereof. In a specific embodiment, the citric acid is used. Although certain of the above-listed acids may have certain pharmacological activities, at certain doses, the encapsulated acid used in the polymersome of the present invention is not aimed at exerting a direct pharmacological or imaging function but is solely used to create the transmembrane pH gradient. The present invention encompasses the use of any one of the above-cited acids, whether or not they also possess certain pharmacological activities. However, in accordance with certain embodiments or aspects of the present invention, the acid may not be an acid, other than any of the above-listed acids, that is known as an antibiotic, anticancer drug, an antihypertensive drug, an antifungal drug, an anxiolytic drug, an anti-inflammatory drug, an immunomodulatory drug, an antiviral drug, or a lipid lowering agent.

Figure 12:
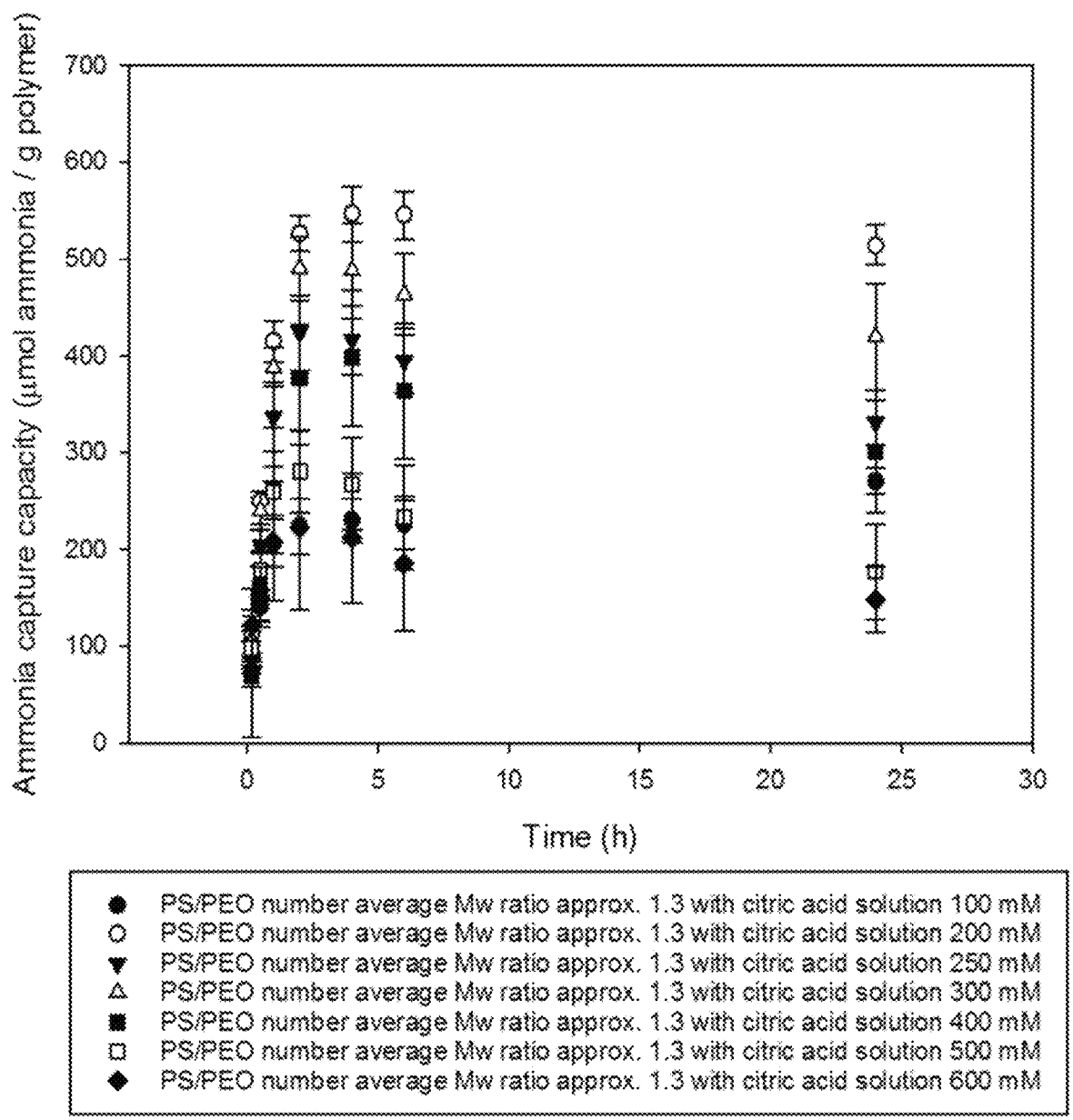
FIG. 12 is a graph showing the in vitro ammonia uptake of transmembrane pH-gradient PS-b-PEO polymersomes with a PS/PEO number average Mw ratio of approximately 1.3 prepared by mixing the polymer-containing organic solvent phase with the aqueous acidic phase using dichloromethane as organic solvent and with varying concentrations of acid (n=3-4, mean and standard deviation).

In specific embodiments, the concentration of acid used in the method may be varied between 50 and 700 mM. When citric acid is used, a citric acid solution of between about 100 mM and 600 mM at an osmolality between 50 and 800 mOsmol/kg is optimally used (see FIG. 12). In another specific embodiment, the osmolality is between 100 and 750 mOsmol/kg. In another specific embodiment, the osmolality is between 100 and 700 mOsmol/kg, in another specific embodiment, the osmolality is between 115 and 700 mOsmol/kg.

The acid within the core is present in a concentration that produces a pH between 1 and 6, when the polymersome is hydrated.

Method of Use

Transmembrane pH-gradient polymersomes of the present invention may be used in the enteral (e.g., oral, intracolonic, rectal) or topical treatment of an ammonia or its methylated analog related disease or disorder, or symptom thereof (e.g., hyperammonemia (enteral) or trimethylaminuria (enteral or topical)) in a subject in need thereof.

As used herein an "ammonia or ammonia methylated analog-associated disease or disorder, or a symptom thereof" includes hyperammonemia (e.g., induced by impaired liver function), hepatic encephalopathy, liver cirrhosis, acute liver failure, acute-on-chronic liver failure, portosystemic bypass, portosystemic shunting, drug-induced hyperammonemia, inborn deficiency in hepatic ammonia metabolism (primary hyperammonemia), inborn deficiency affecting hepatic ammonia metabolism (secondary hyperammonemia), trimethylaminuria, a TMA-associated cardiovascular disease (e.g., atherosclerosis, peripheral artery disease, coronary artery disease, myocardial infarction), a TMA-associated kidney disease (e.g., renal tubulointerstitial fibrosis and dysfunction, renal insufficiency, chronic kidney disease-associated mortality) or TMA-associated bacterial vaginosis, or a symptom thereof. As used herein in relation to an ammonia or its methylated analog-associated disease or disorder, the terms "a symptom thereof" include malodor (from e.g., skin and/or urine and/or expired air and/or vagina).

The polymersomes may be administered enterally to the subject in different dosage forms e.g., could be dispersed in an aqueous medium (e.g., water, juice) or taken in their dried form as is by the subject (e.g., capsule, tablet). The polymersomes will be excreted via the feces. The polymersomes may also be administered topically to the subject in different dosage forms e.g., could be dispersed in a topical formulation such as an aqueous solution, a foam, a gel, or an emulsion (e.g., o/w or w/o) (e.g., lotion, cream).

As used herein the terms "subject" or "subject in need thereof" refer to a subject who would benefit from receiving an effective amount of the polymersomes or composition thereof of the present invention. It refers to an animal, mammal and to a human in a specific embodiment. The compositions of the present invention may also be used for veterinary applications and be used in pets or other animals (e.g., pets such as cats, dogs, horses, etc.; and cattle, fishes, swine, poultry, etc.). In a specific embodiment, the subject suffers from hyperammonemia (e.g., induced by impaired liver function). In specific embodiment, the subject suffers from hepatic encephalopathy, liver cirrhosis, acute liver failure, acute-on-chronic liver failure, portosystemic bypass, portosystemic shunting, drug-induced hyperammonemia, inborn deficiencies in hepatic ammonia metabolism (primary hyperammonemia), or inborn deficiencies affecting hepatic ammonia metabolism (secondary hyperammonemia), or any symptom thereof. In another specific embodiment, the subject suffers from trimethylaminuria, a TMA-associated cardiovascular disease, a TMA-associated kidney disease, a TMA-associated bacterial vaginosis, or any symptom thereof.

Compositions

The polymersomes of the present invention may be stored as a liquid (e.g., liquid suspension), semi solid (e.g., emulsion such as lotion or cream) or solid form (e.g., powder, capsule, tablet, suppository).

The present invention also relates to the use of the polymersomes and/or compositions in the preparation of a medicament.

The present invention also relates to pharmaceutical compositions comprising the above polymersomes of the invention.

Without being so limited, the polymersomes or compositions thereof of the invention may be administered through an enteral route (i.e. through the gastrointestinal tract) or topical route. When the oral route is used for example, the polymersomes can be in the form of e.g., tablets, coated tablets, hard or soft gelatin capsules or suspensions. When the rectal/intracolonic route for example, the polymersomes can be in the form of e.g., suppositories or suspensions. When the topical route is used for example, the polymersomes can be in the form of an emulsion (e.g., o/w or w/o) such as a lotion or cream, gels and foams, or an aqueous solution.

The compositions of the invention can contain a pharmaceutically acceptable carrier including, without limitation, aqueous or non-aqueous solutions. Examples of non-aqueous solvents include, without limitation, propylene glycol, polyethylene glycol, emulsions, etc. Aqueous carriers include, without limitation, water, alcohol, saline, and buffered solutions. Pharmaceutically acceptable carriers also can include physiologically acceptable aqueous vehicles (e.g., sugar solutions, saline) or other known carriers appropriate for the enteral or topical routes.

For the preparation of tablets, coated tablets, or hard gelatin capsules, the polymersomes of the present invention may be admixed with any known pharmaceutically inert, inorganic or organic excipient and/or carrier. Examples of suitable excipients/carriers include lactose, maize starch or derivatives thereof, talc or stearic acid or salts thereof.

For the preparation of suspensions (liquid forms are suspensions because polymersomes are not soluble in water), excipients which may be used include for example water, polyols, saccharose, invert sugar and glucose.

For the preparation of emulsion, the polymersomes of the present invention may be admixed with any known pharmaceutically inert, inorganic or organic excipient and/or carrier. Examples of suitable excipients/carriers include water, surfactants (e.g., polysorbates, sorbitan esters, sodium lauryl sulfate, etc.), oils (e.g., mineral or vegetable oils).

The compositions of the present invention may also contain preserving agents, stabilizing agents, wetting agents, sweeteners, colorants, odorants, salts for the variation of osmotic pressure, buffers, or antioxidants. They may also contain other therapeutically active agents.

It is a prerequisite that all excipients used in the manufacture of the compositions of the present invention, such as carriers, are non-toxic and more generally pharmaceutically acceptable. As used herein, "pharmaceutically acceptable" such as pharmaceutically acceptable carrier, excipient, etc., means pharmacologically acceptable and substantially non-toxic to the subject to which the particular composition of the present invention is administered.

Combination Therapy

Polymersomes of the invention can also be administered in a combination therapy, i.e., combined with at least one other active agent or therapy for simultaneous or sequential administration. The combination therapy can include a polymersome or composition of the present invention combined with at least one other agent or therapy for the ammonia or its methylated analog-associated disease or disorder or symptom thereof.

For example, the combination therapy can include a polymersome or composition of the present invention combined with at least one other anti-hyperammonemia agent or therapy or with a medicament or therapy used for the prevention or treatment of at least one other symptom of a disease or condition of the subject having hyperammonemia. In this context, examples of active ingredients or therapies that may be administered in combination (simultaneously or sequentially) with the polymersomes or compositions of the present invention include lactulose, rifaximin, glycerol phenylbutyrate, lactitol, a branched-chain amino acid, neomycin, metronidazole, probiotic, a glutaminase inhibitor, L-ornithine-L-aspartate, hemodialysis, peritoneal dialysis, sodium phenylbutyrate, sodium phenylacetate/sodium benzoate, or carglumic acid.

As another example, the combination therapy can include a polymersome or composition of the present invention combined with at least one other anti-trimethylaminuria agent or therapy or with a medicament or therapy used for the prevention or treatment of at least one other symptom of a disease or condition of the subject having trimethylaminuria. In this context, examples of active ingredients or therapies that may be administered in combination (simultaneously or sequentially) with the polymersomes or compositions of the present invention include certain orally applied antibiotics (e.g., neomycin, metronidazole), activated charcoal, acidic soap.

Kits

Also within the scope of the invention are kits comprising at least one type of polymersomes or compositions of the present invention and instructions for their use. The kit can further contain a least one additional reagent, or one or more additional types of polymersomes of the invention. Kits typically include a label indicating the intended use of the contents of the kit. The term label includes any writing, or recorded material supplied on or with the kit, or which otherwise accompanies the kit. The kit may further comprise one or more container(s), reagent(s), administration device(s).

Dosage

The dosages in which the polymersomes or compositions thereof of the invention are administered will depend on many factors including the age, other medications taken by subject (e.g., for other diseases or conditions) and other clinically relevant factors. Typically, the amount of the polymersomes or compositions thereof of the invention contained within a single dose will be an amount that effectively treats the ammonia or its methylated analog associated disease or disorder or symptom thereof (e.g., hyperammonemia, trimethylaminuria) without inducing significant toxicity.

The effective amount of the polymersomes or compositions thereof of the invention may also be measured directly. The effective amount may be given daily or weekly or fractions thereof. Typically, the dose of polymersomes of the present invention expressed in terms of mass of block copolymer ranges from about 1 mg up to about 500 mg per kg of body weight per day (e.g., 1 mg, 10 mg, 50 mg, 100 mg, or 250 mg/kg of body weight per day). Dosages may be provided in either a single or multiple dosage regimen. For example, in some embodiments the effective amount may range from about 250 mg to about 500 mg per day, from about 500 mg to about 1000 mg per day, about 1 gram per day, about 2-12 grams per day, about 14 g to about 86 grams of the composition per week, etc.

The present invention encompasses any combination of the herein-described block copolymers, or compositions comprising same, in the herein-described ratios, prepared using the herein-described solvent and acid or acid solutions using the above-described organic phase and water phase mixing techniques.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

The present invention is illustrated in further details by the following non-limiting examples.

Example 1: In Vitro Ammonia Uptake of Liposomes Prepared Using a Film Hydration Method Liposome Preparation. Liposomes composed of (i) 1,2-dipalmitoyl-sn-glycero-3-phosphocholine (DPPC) or 1,2-distearoyl-sn-glycero-3-phosphocholine (DSPC), (ii) cholesterol and (iii) 1,2-distearoyl-sn-glycero-3-phosphoethanol-amine-N-[methoxy(PEO)-2000] (DSPE-PEO) at 54:45:1 mol % were prepared by the film hydration method. Stock solutions of DPPC 36.7 mg/mL, DSPC 39.5 mg/mL, cholesterol 19.3 mg/mL, and DSPE-PEO 13.9 mg/mL were prepared in chloroform.

For the DSPC liposomes, 8.2 mg cholesterol, 20.2 mg DSPC, and 1.3 mg DSPE-PEO were added as chloroform stock solutions to a glass vial. For the DPPC liposomes, 19.7 mg DPPC, 8.7 mg cholesterol, and 1.4 mg DSPE-PEO, were added as chloroform stock solutions to a glass vial. The organic solvent was subsequently removed by nitrogen flow for 2 h and storage under vacuum overnight. The dried film was hydrated with 1 mL of citric acid solution 250 mM at pH 2.0 at 300 mOsmol/kg (lipid concentration=29.8 mg/mL) while heating to 55° C. and slowly mixing until the lipid film was not visible any more. The liposomes encapsulate the citric acid solution of pH 2. At the end of the process, there is citric acid inside and outside the liposomes.

In vitro ammonia uptake. The transmembrane pH-gradient was generated in side-by-side diffusion cells maintained at 37° C. by dilution in phosphate buffer (final concentration 50 mM) under adjustment to pH 6.8 and 300 mOsmol/kg in the absence and presence of the bile salts sodium cholate (SC) and sodium deoxycholate (SDC, both 25 mM). The dual-chamber system was separated by a polycarbonate membrane (pore size=50 nm), physically isolating the liposomes on one side. The lipid and the ammonia concentrations within the diffusion cells were 1.75 mg/mL and 1.5 mM, respectively. At the allotted time, aliquots of 40 μL were taken from the liposome-free compartment and the ammonia concentration was determined by the Berthelot reaction using equivolumetric amounts of alkaline sodium hypochlorite solution and phenol-nitroprusside solution. The ammonia capture capacity was quantified using equation 1:

$$\text{Ammonia capture capacity} = \frac{\text{Encapsulated ammonia [μmol]}}{\text{Total lipid mass [g]}} = \frac{\text{Total ammonia [μmol]} - \text{Free ammonia [μmol]}}{\text{Total lipid mass [g]}} \quad \text{Eq. 1}$$

The liposome formulations were capable of capturing ammonia in phosphate buffer but not in bile salt-containing medium (n=3). Results are reported in FIG. 1. Each point in the graph represents the average of the group n=3 and the error bars represent the standard deviation.

Example 2: In Vitro Ammonia Uptake of PBD-b-PEO Polymersomes with a PBD/PEO Number Average Mw Ratio Approximately (i.e. Rounded to One Decimal Place) 1.7 Prepared by Mixing the Polymer-Containing Organic Solvent Phase with the Aqueous Acidic Phase Using Dichloromethane as Organic Solvent Polymersome Preparation. PBD-b-PEO polymersomes were produced using an oil-in-water (o/w) emulsion method. More particularly, sixty mg of PBD-b-PEO (PBD/PEO number average molecular weight (Mw) ratio of approximately 1.7 (i.e., 2500 g/mol/1500 g/mol), PBD(2500)-b-PEO(1500)) were dissolved in 100 μL of dichloromethane. The polymer dichloromethane solution (polymer-containing organic solvent phase, i.e. oil phase) was added dropwise to 1 mL citric acid solution 250 mM at pH 2.0 at 300 mOsmol/kg (acidic aqueous phase), under sonication (amplitude 70, cycle 0.75, duration 3 minutes) in an ice bath for 3 minutes so as to form an emulsion having a 9% (v/v) solvent/aqueous phase ratio. The organic solvent was evaporated using a rotary evaporator for at least 5 minutes at 40° C. The polymersomes encapsulate the citric acid solution of pH 2. At the end of the process, there is citric acid inside and outside the polymersomes.

In Vitro Ammonia Uptake. The in vitro ammonia uptake was studied by means of side-by-side diffusion cells as described in Example 1 with a polymer concentration of 1.75 mg/mL. The ammonia capture capacity was quantified using equation 2:

$$\text{Ammonia capture capacity} = \frac{\text{Encapsulated ammonia [μmol]}}{\text{Total polymer mass [g]}} = \frac{\text{Total ammonia [μmol]} - \text{Free ammonia [μmol]}}{\text{Total polymer mass [g]}} \quad \text{Eq. 2}$$

Figure 2:
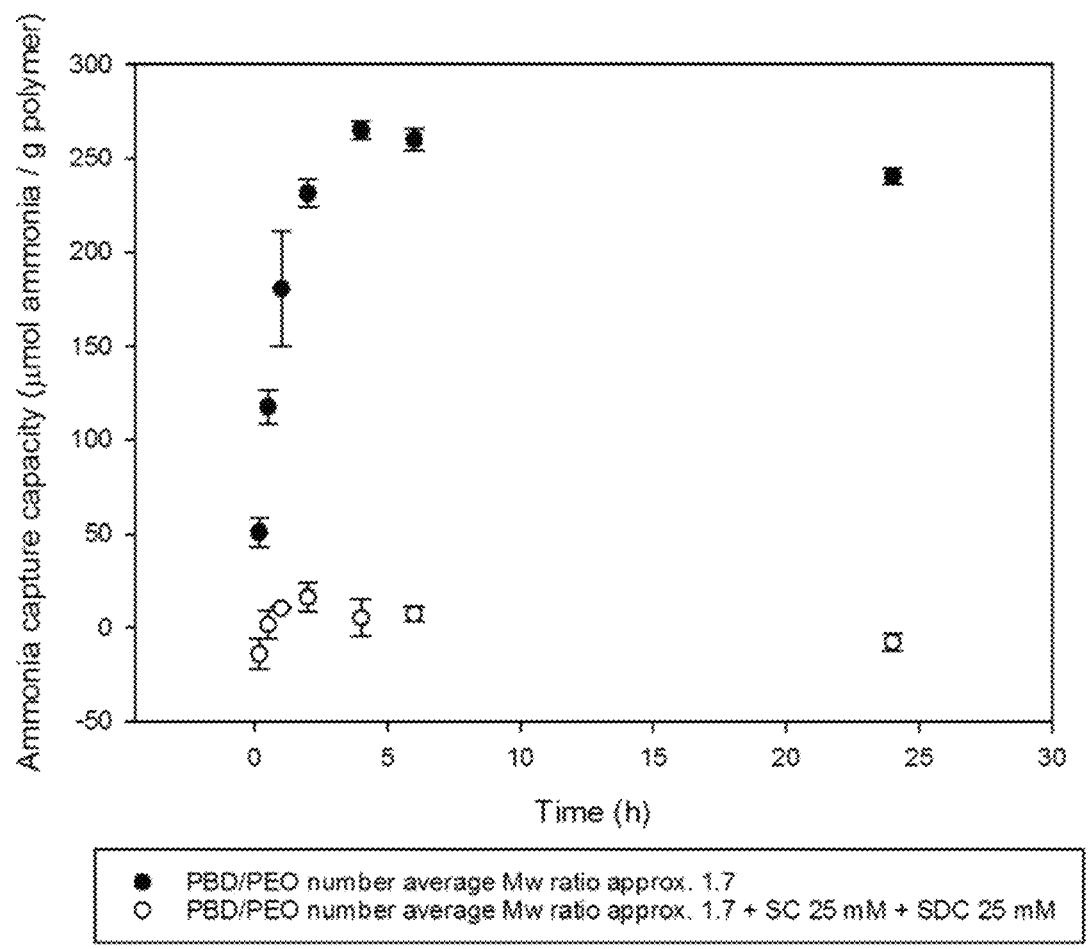
FIG. 2 is a graph showing the in vitro ammonia uptake of transmembrane pH-gradient PBD-b-PEO polymersomes with a PBD/PEO number average Mw ratio of approximately 1.7 prepared by mixing the polymer-containing organic solvent phase with the aqueous acidic phase using dichloromethane as organic solvent (n=3, mean and standard deviation).

The PBD PEO polymersomes were capable of capturing ammonia in phosphate buffer but not in bile salt-containing medium (n=3). Results are reported in FIG. 2. Each point in the graph represents the average of the group n=3 and the error bars represent the standard deviation.

Example 3: In Vitro Ammonia Uptake of PMOXA-b-PDMS-b-PMOXA Polymersomes with a PDMS/PMOXA Number Average Mw Ratio of Approximately 2.4 Prepared by Mixing the Polymer-Containing Organic Solvent Phase with the Aqueous Acidic Phase Using Dichloromethane as Organic Solvent Polymersome Preparation. PMOXA-b-PDMS-b-PMOXA polymersomes (PDMS/PMOXA number average Mw ratio of approximately 2.4 (PMOXA(520)-b-PDMS(2530)-b-PMOXA(520))) were produced as described in Example 2.

In Vitro Ammonia Uptake. The in vitro ammonia uptake was studied by means of side-by-side diffusion cells as described in Example 2 without bile salts (i.e. phosphate buffer only).

Figure 3:
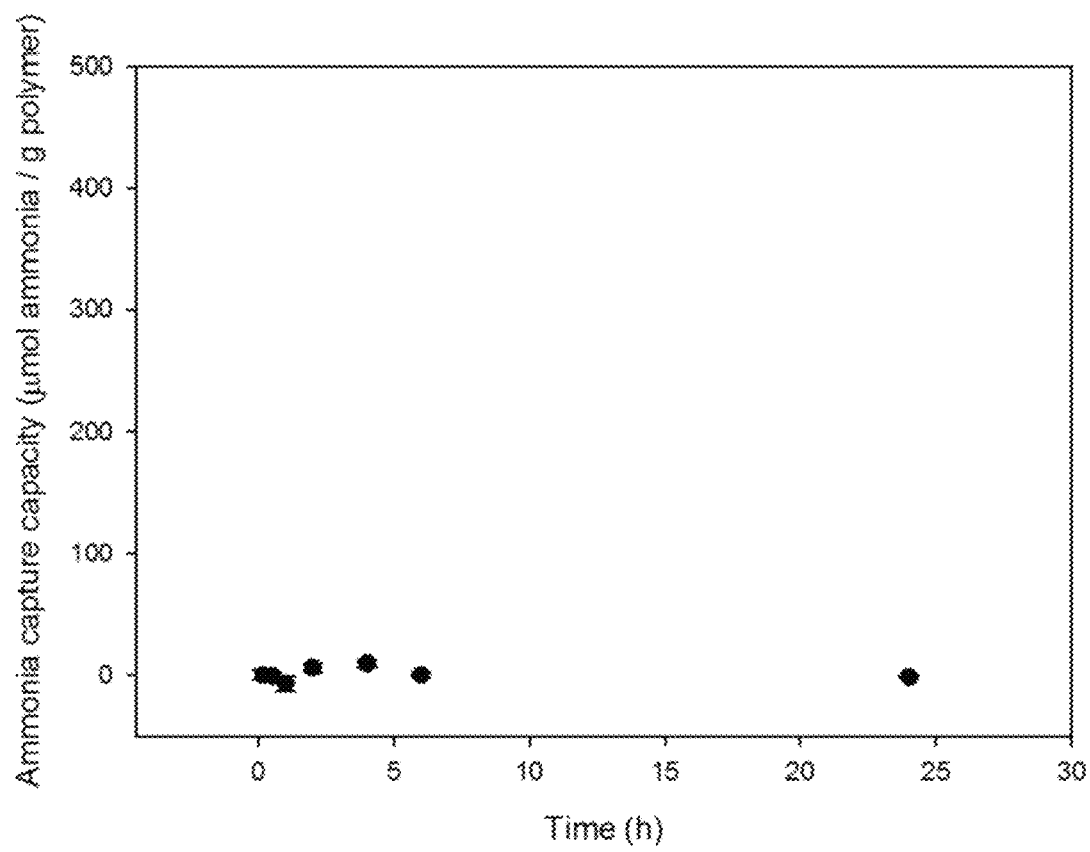
FIG. 3 is a graph showing the in vitro ammonia uptake of transmembrane pH-gradient PMOXA-b-PDMS-b-PMOXA polymersomes with a PDMS/PMOXA number average Mw ratio of approximately 2.4 prepared by mixing the polymer-containing organic solvent phase with the aqueous acidic phase using dichloromethane as organic solvent. (n=3, mean and standard deviation).

The PMOXA PDMS PMOXA polymersomes were not capable of capturing ammonia in bile salt-free medium (i.e. phosphate buffer only) (n=3). Results are reported in FIG. 3. Each point in the graph represents the average of the group n=3 and the error bars represent the standard deviation.

Example 4: In Vitro Ammonia Uptake of PS-b-PEO Polymersomes with PS/PEO Number Average Mw Ratios of Approximately 1.3 or 2.5 Prepared Using a Film Hydration Method Polymersome Preparation. PS-b-PEO polymersomes were produced using a film hydration method. More particularly, 29.8 mg PS-b-PEO (PS/PEO number average Mw ratios of approximately 1.3 (PS(2600)-b-PEO(2000)) or of approximately 2.5 (PS(5150)-b-PEO(2060))) were dissolved in 100 μL of dichloromethane and added to a glass vial. The organic solvent was subsequently removed by nitrogen flow for 2 h and storage under vacuum overnight. The dried film was hydrated with 1 mL of citric acid solution 250 mM at pH 2.0 at 300 mOsmol/kg under heating to 65° C. and sonication for 1.25 h.

In Vitro Ammonia Uptake. The in vitro ammonia uptake was studied by means of side-by-side diffusion cells as described in Example 3 (i.e. phosphate buffer only).

Figure 4:
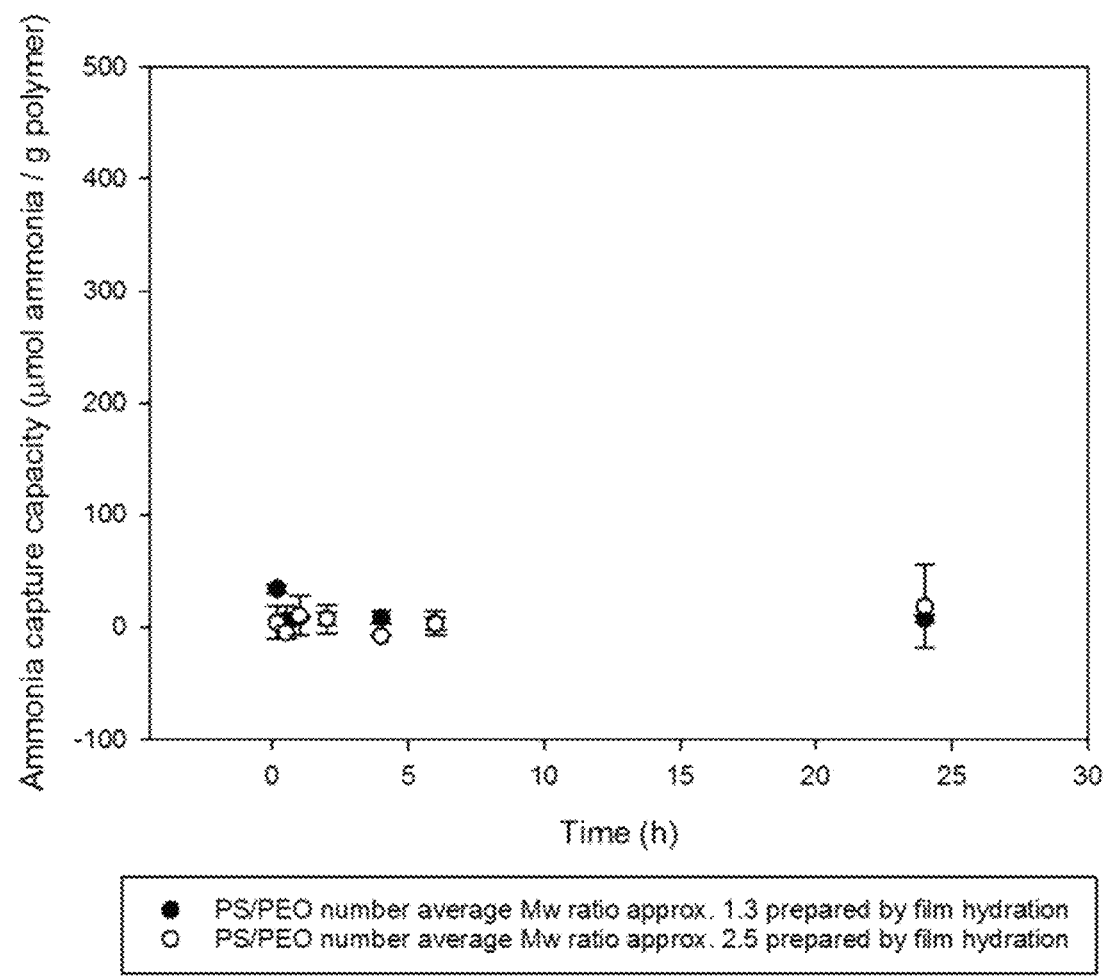
FIG. 4 is a graph showing the in vitro ammonia uptake of transmembrane pH-gradient PS-b-PEO polymersomes with PS/PEO number average Mw ratios of approximately 1.3 or 2.5 prepared using a film hydration method (n=3, mean and standard deviation).

The PS PEO polymersomes were not capable of capturing ammonia in bile salt-free medium (i.e. phosphate buffer only) (n=3). Results are presented in FIG. 4. Each point in the graph represents the average of the group n=3 and the error bars represent the standard deviation.

Example 5: In Vitro Ammonia Uptake at High Bile Salt Concentrations of PS-b-PEO Polymersomes with a PS/PEO Number Average Mw Ratio of Approximately 1.0 Prepared by Mixing the Polymer-Containing Organic Solvent Phase with the Aqueous Acidic Phase Using Dichloromethane as Organic Solvent Polymersome Preparation. PS-b-PEO polymersomes (PS/PEO number average Mw ratio of approximately 1.0 (PS(1970)-b-PEO(2000))) were produced as described in Example 2.

In Vitro Ammonia Uptake. The in vitro ammonia uptake was studied by means of side-by-side diffusion cells as described in Example 2 with a modified bile salts composition (SC 30 mM, SDC 30 mM, sodium taurocholate (STC) 30 mM, final pH 6.8 and osmolality 300 mOsmol/kg). This bile salt concentration corresponds to twice the physiological concentration.

Figure 5:
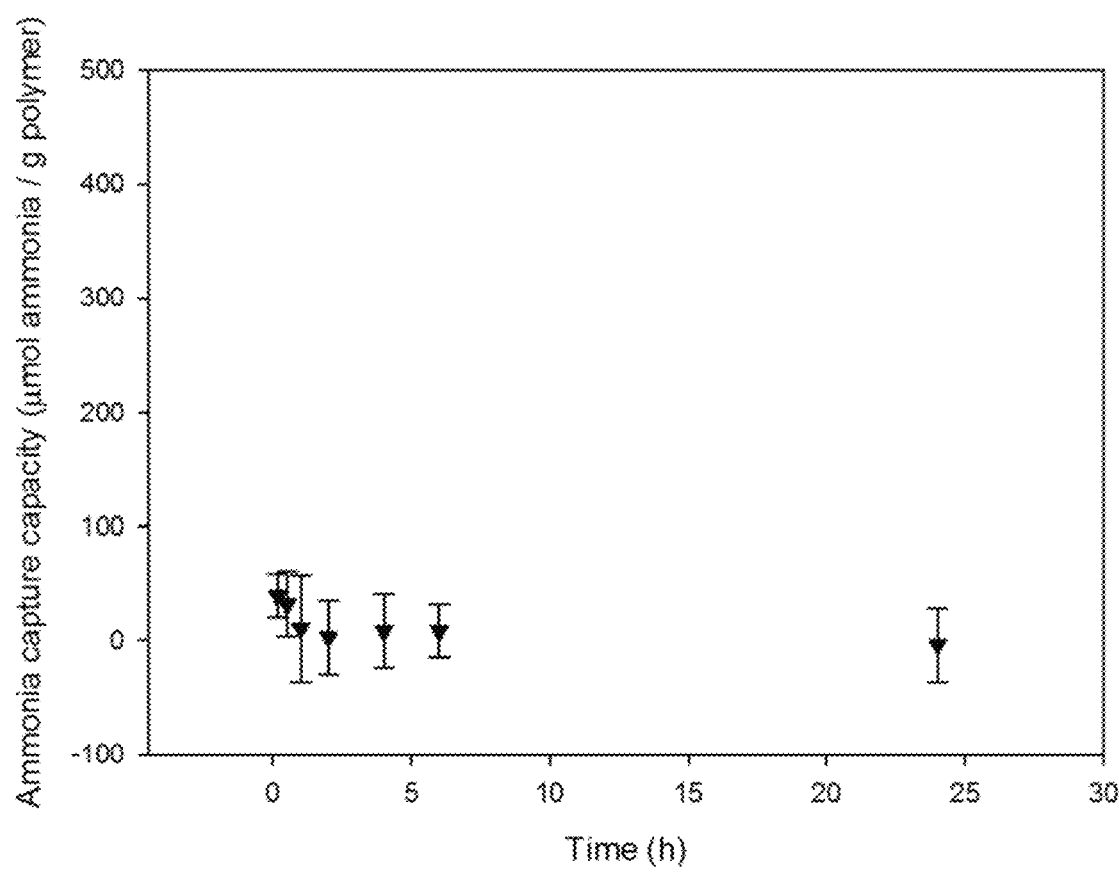
FIG. 5 is a graph showing the in vitro ammonia uptake at high bile salt concentrations of transmembrane pH-gradient PS-b-PEO polymersomes with a PS/PEO number average Mw ratios of 1.0 prepared by mixing the polymer-containing organic solvent phase with the aqueous acidic phase using dichloromethane as organic solvent (n=3, mean and standard deviation).

The PS PEO polymersomes were not capable of capturing ammonia in bile salt-containing medium (n=3). Results are presented in FIG. 5. Each point in the graph represents the average of the group n=3 and the error bars represent the standard deviation.

Example 6: In Vitro Ammonia Uptake at High Bile Salt Concentrations of PS-b-PEO Polymersomes with PS/PEO Number Average Mw Ratios Between Approximately 1.3 and 2.8 Prepared by Mixing the Polymer-Containing Organic Solvent Phase with the Aqueous Acidic Phase Using Dichloromethane or Toluene as Organic Solvent Polymersome Preparation. PS-b-PEO polymersomes (PS/PEO number average Mw ratios of approximately 1.3 (PS(2600)-b-PEO(2000)), approximately 1.6 (PS(3150)-b-PEO(2000)), approximately 1.8 (PS(3570)-b-PEO(2000)), approximately 2.0 (PS(3900)-b-PEO(2000)), or approximately 2.5 (PS(5150)-b-PEO(2060))) were produced as described in Example 2. PS PEO polymersomes (PS/PEO number average Mw ratio of approximately 2.8 (PS(6000)-b-PEO(2180))) were prepared as described in Example 2 but using toluene instead of dichloromethane as an organic solvent, and using a lower polymer amount (twenty mg).

In Vitro Ammonia Uptake. The in vitro ammonia uptake was studied by means of side-by-side diffusion cells as described in Example 5 for PS PEO polymersomes with a PS/PEO number average Mw ratio of approximately 1.3 to 2.5. PS PEO polymersomes (PS/PEO number average Mw ratio of approximately 2.8 (PS(6000)-b-PEO(2180))) were evaluated as described in Example 5 with a modified phosphate concentration (25 mM) at 440 mOsmol/kg and pH 6.8.

Figure 6:
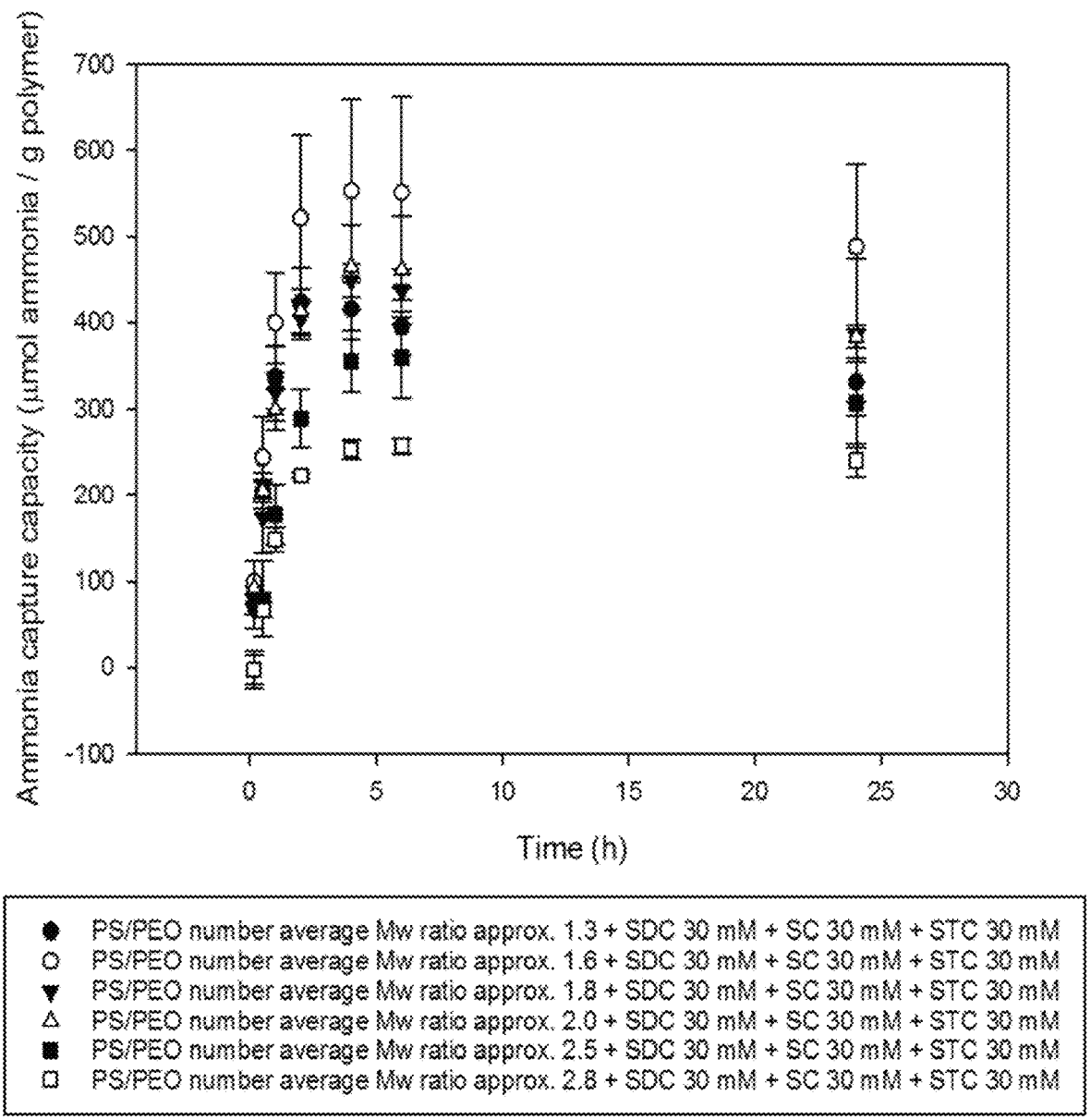
FIG. 6 is a graph showing the in vitro ammonia uptake at high bile salt concentrations of transmembrane pH-gradient PS-b-PEO polymersomes with PS/PEO number average Mw ratios between approximately 1.3 and 2.8 prepared by mixing the polymer-containing organic solvent phase with the aqueous acidic phase using dichloromethane or toluene as organic solvent (n=3, mean and standard deviation).

The PS PEO polymersomes were capable of capturing ammonia in bile salt-containing medium (n=3). Results are presented in FIG. 6. Each point in the graph represents the average of the group n=3 and the error bars represent the standard deviation.

Example 7: In Vitro Ammonia Uptake at High Bile Salt Concentrations of PS-b-PEO Polymersomes with a PS/PEO Number Average Mw Ratio of Approximately 3.8 Prepared by Mixing the Polymer-Containing Organic Solvent Phase with the Aqueous Acidic Phase Using Dichloromethane as Organic Solvent Polymer Synthesis. PS-b-PEO was synthesized by atom transfer radical polymerization (ATRP). First, commercially available PEO monomethyl ether (2150 g mol$^{-1}$) was reacted with bromoisobutyryl bromide (5.0 eq) and triethylamine (5.0 eq) in THF, to yield a macroinitiator. In the subsequent polymerization reaction, this macroinitiator (1.0 eq), CuBr (1.6 eq), and 4,4'-dinonyl-2,2'-dipyridyl (1.4 eq) were transferred to a Schlenk flask and degassed by vacuum-argon cycles. Styrene (70 eq) was added in a separate flask and degassed, using argon, before being transferred to the reaction flask. The reaction was conducted at 115° C. for 24 hours. Purification of the final product was achieved by passing the solution through a column of basic alumina, followed by two precipitations in hexane. The number average molecular weight of the polymer was determined by $^1$H NMR spectroscopy, comparing the integral value of the PEG backbone to the aromatic polystyrene peaks, resulting in a polymer composition of PS(8100)-b-PEO(2150).

Polymersome Preparation. PS-b-PEO polymersomes (PS/PEO number average Mw ratio of approximately 3.8 (PS(8100)-b-PEO(2150))) were produced as described in Example 2.

In Vitro Ammonia Uptake. The in vitro ammonia uptake was studied by means of side-by-side diffusion cells as described in Example 5 with a modified polymer concentration of 1.24 mg/mL.

Figure 7:
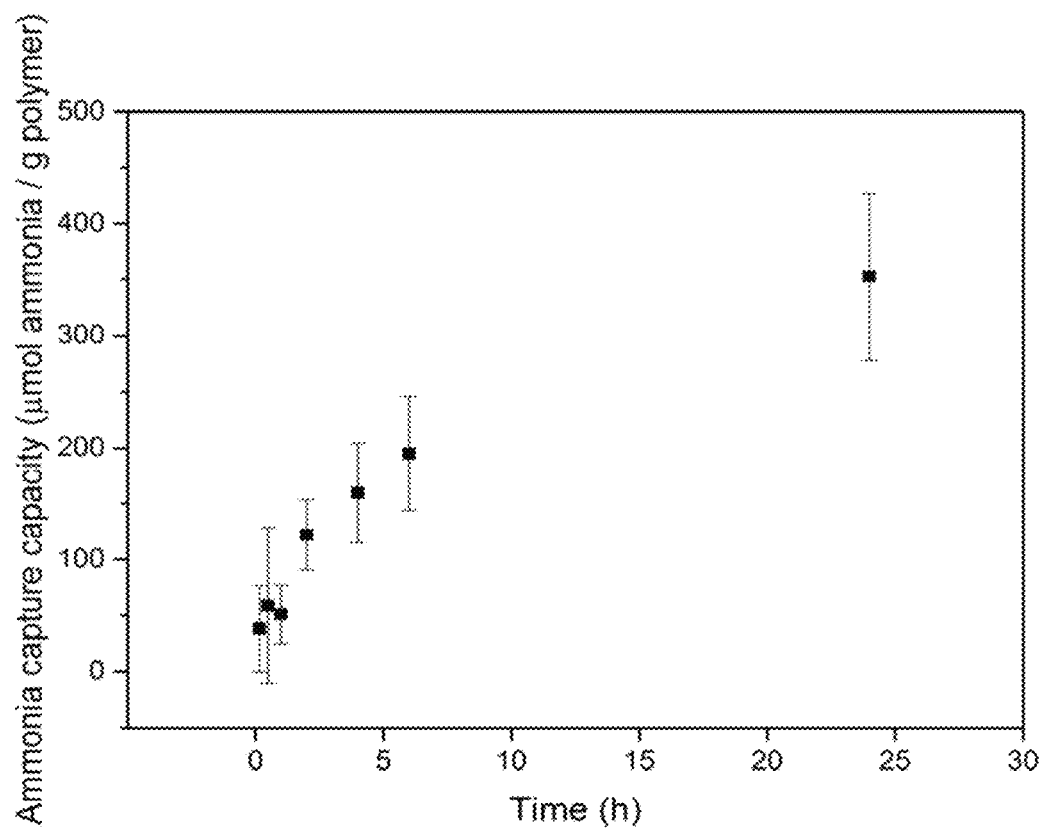
FIG. 7 is a graph showing the in vitro ammonia uptake at high bile salt concentrations of transmembrane pH-gradient PS-b-PEO polymersomes with PS/PEO number average Mw ratios of approximately 3.8 prepared by mixing the polymer-containing organic solvent phase with the aqueous acidic phase using dichloromethane as organic solvent (n=3, mean and standard deviation).

The PS PEO polymersomes were capable of capturing ammonia in bile salt-containing medium (n=3). Results are presented in FIG. 7. Each point in the graph represents the average of the group n=3 and the error bars represent the standard deviation.

Example 8: In Vitro Ammonia Uptake at High Bile Salt Concentrations of PS-b-PEO Polymersomes with a PS/PEO Number Average Mw Ratio of Approximately 1.3 Prepared by Mixing the Polymer-Containing Organic Solvent Phase with the Aqueous Acidic Phase Using Chloroform as Organic Solvent Polymersome Preparation. PS-b-PEO polymersomes (PS/PEO number average Mw ratio of approximately 1.3 (PS(2600)-b-PEO(2000))) were produced as described in Example 2 using chloroform instead of dichloromethane as organic solvent.

In Vitro Ammonia Uptake. The in vitro ammonia uptake was studied by means of side-by-side diffusion cells as described in Example 5.

Figure 8:
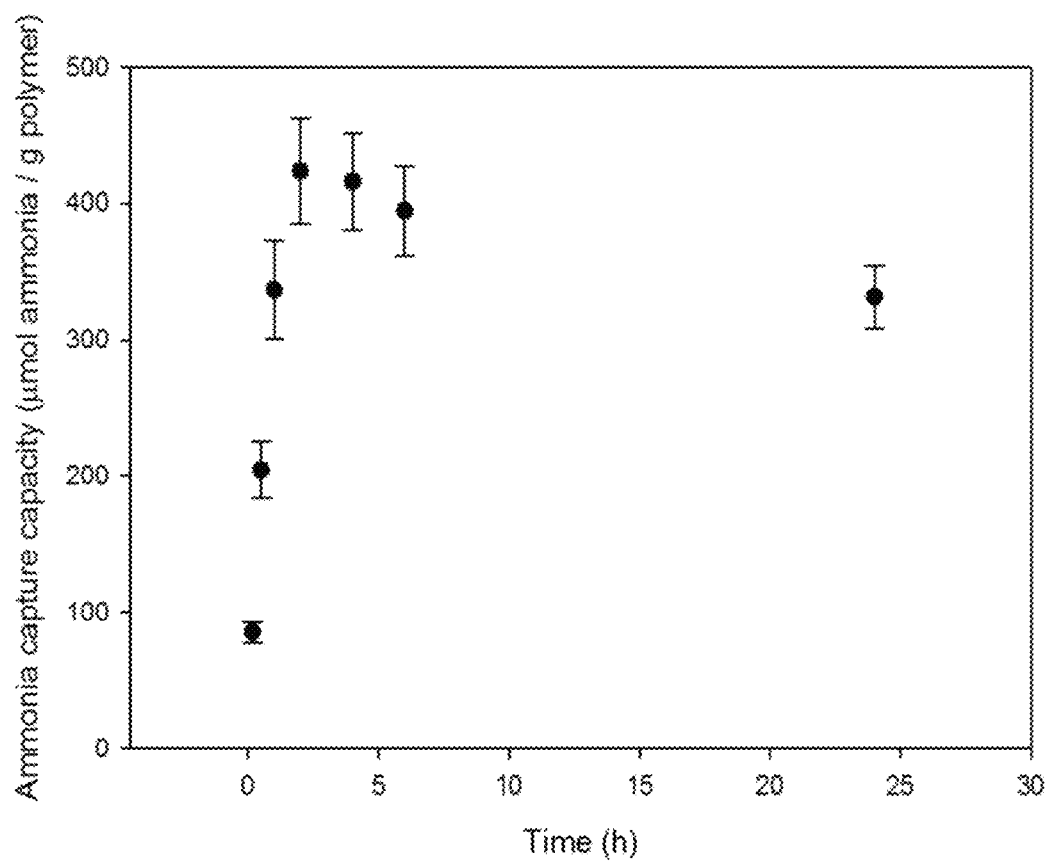
FIG. 8 is a graph showing the in vitro ammonia uptake at high bile salt concentrations of transmembrane pH-gradient PS-b-PEO with a PS/PEO number average Mw ratio of approximately 1.3 prepared by mixing the polymer-containing organic solvent phase with the aqueous acidic phase using chloroform as organic solvent (n=3, mean and standard deviation).

The PS PEO polymersomes were capable of capturing ammonia in bile salt-containing medium (n=3). Results are presented in FIG. 8. Each point in the graph represents the average of the group n=3 and the error bars represent the standard deviation.

Example 9: In Vitro Ammonia Uptake in Hypo- and Hyperosmolar Conditions of PS-b-PEO Polymersomes with PS/PEO Number Average Mw Ratios of Approximately 1.3 or 2.5 Prepared by Mixing the Polymer-Containing Organic Solvent Phase with the Aqueous Acidic Phase Using Dichloromethane as Organic Solvent Polymersome Preparation. PS-b-PEO polymersomes (PS/PEO number average Mw ratios of approximately 1.3 (PS(2600)-b-PEO(2000)) or of approximately 2.5 (PS(5150)-b-PEO(2060))) were produced as described in Example 2.

In Vitro Ammonia Uptake. The in vitro ammonia uptake was studied by means of side-by-side diffusion cells as described in Example 5 with modified buffers at pH 6.8

(hypoosmolar conditions: phosphate buffer 10 mM containing SC 25 mM and SDC 25 mM, final osmolality 160 mOsmol/kg; hyperosmolar conditions: phosphate buffer 50 mM containing SC 30 mM, SDC 30 mM, and STC 30 mM under addition of sodium chloride reaching a final osmolality of 620 mOsmol/kg, i.e. extreme conditions more drastic than those found in G.I. tract in physiological conditions).

Figure 9:
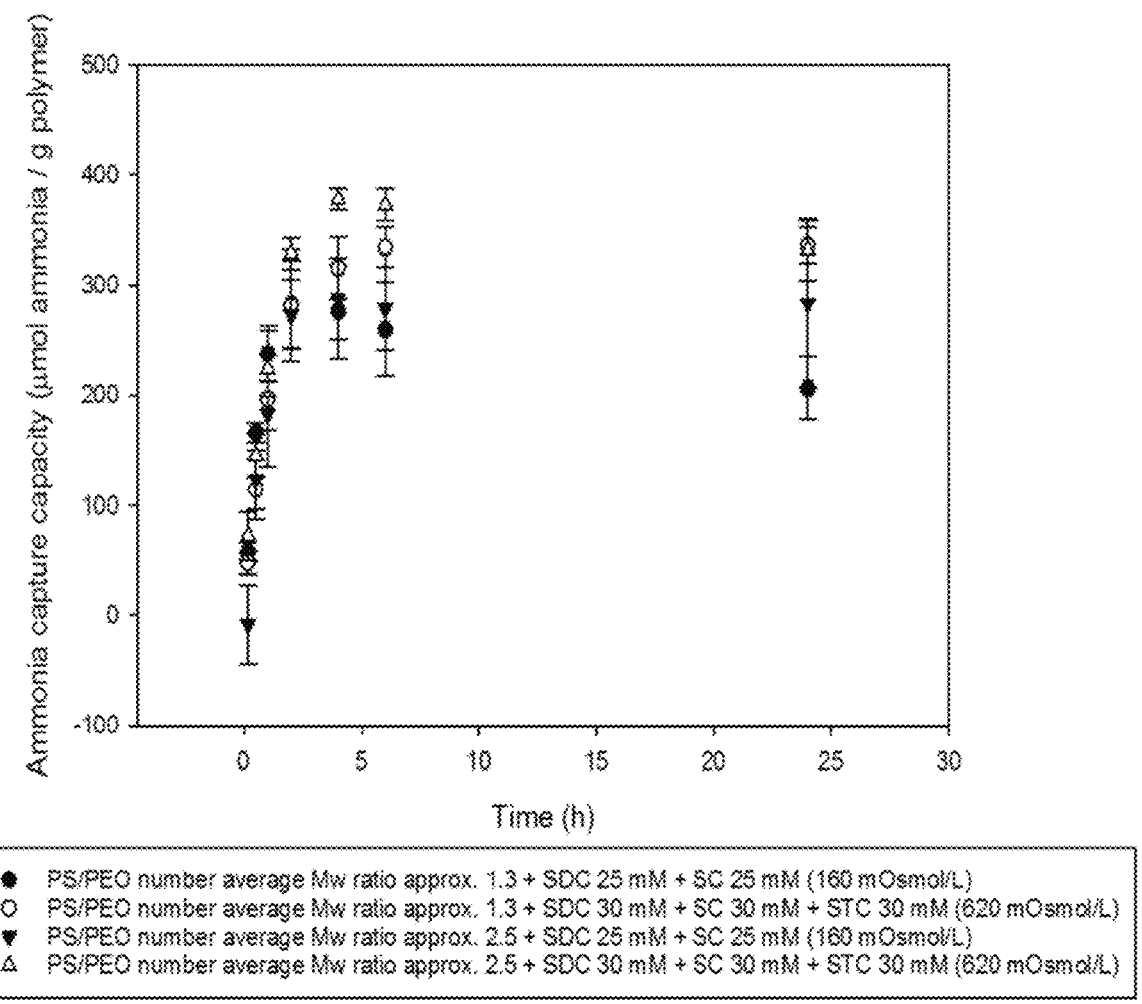
FIG. 9 is a graph showing the in vitro ammonia uptake in hypo- and hyperosmolar conditions of transmembrane pH-gradient PS-b-PEO polymersomes with PS/PEO number average Mw ratios of approximately 1.3 or 2.5 prepared by mixing the polymer-containing organic solvent phase with the aqueous acidic phase using dichloromethane as organic solvent (n=3, mean and standard deviation).

The PS PEO polymersomes were capable of capturing ammonia in bile salt-containing media under hypo- and hyperosmolar conditions (n=3). Results are presented in FIG. 9. Each point in the graph represents the average of the group n=3 and the error bars represent the standard deviation.

Example 10: In Vitro Ammonia Uptake in the Presence of Digestive Enzymes of PS-b-PEO Polymersomes with a PS/PEO Number Average Mw Ratio of Approximately 2.5 Prepared by Mixing the Polymer-Containing Organic Solvent Phase with the Aqueous Acidic Phase Using Dichloromethane as Organic Solvent Polymersome Preparation. PS-b-PEO polymersomes (PS/PEO number average Mw ratio of approximately 2.5 (PS (5150)-b-PEO(2060)) were produced as described in Example 2.

In Vitro Ammonia Uptake. The in vitro ammonia uptake was studied by means of side-by-side diffusion cells as described in Example 5 with a modified buffer at pH 6.8 and 300 mOsmol/kg (phosphate buffer 50 mM, SC 12.5 mM, SDC 12.5 mM, trypsin from porcine pancreas 1 mg/mL (approximately 10 000 units/mL), α-chymotrypsin from bovine pancreas (Type II) 1 mg/mL (approximately 40 units/mL), lipase from porcine pancreas (Type II) 3 mg/mL (approximately 300 units/mL)). The activity of the enzymes corresponds to the protease and lipase activity in simulated intestinal fluid United States Pharmacopeia (USP 39-NF 34). The lower bile salt concentration than that used in Example 5 was selected to ensure enzymatic activity, and the kinetics was limited to four hours to avoid interferences by degradation products of the digestive enzymes.

Figure 10:
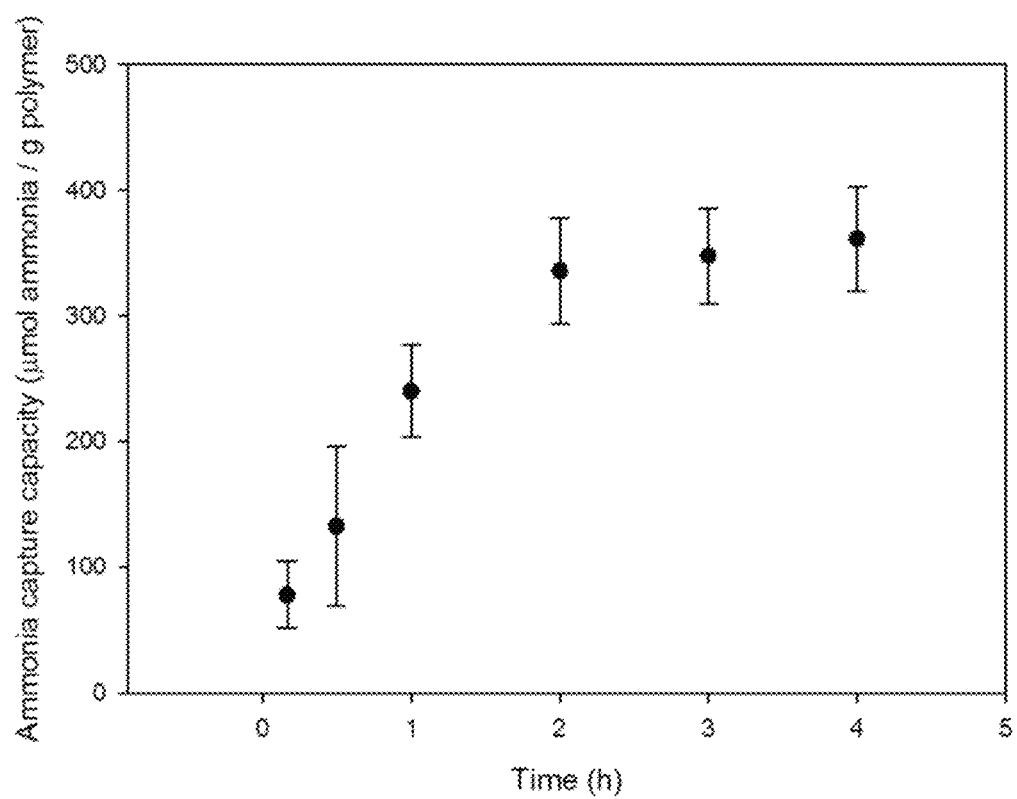
FIG. 10 is a graph showing the in vitro ammonia uptake in the presence of digestive enzymes of transmembrane pH-gradient PS-b-PEO polymersomes with a PS/PEO number average Mw ratio of approximately 2.5 prepared by mixing the polymer-containing organic solvent phase with the aqueous acidic phase using dichloromethane as organic solvent (n=3, mean and standard deviation).

The PS PEO polymersomes were capable of capturing ammonia in bile salt- and digestive enzyme-containing medium (n=3). Results are presented in FIG. 10. Each point in the graph represents the average of the group n=3 and the error bars represent the standard deviation.

Example 11: In Vitro Ammonia Uptake at High Potassium Concentrations of PS-b-PEO Polymersomes with a PS/PEO Number Average Mw Ratio of Approximately 1.3 Prepared by Mixing the Polymer-Containing Organic Solvent Phase with the Aqueous Acidic Phase Using Dichloromethane as Organic Solvent Polymersome Preparation. PS-b-PEO polymersomes (PS/PEO number average Mw ratio of approximately 1.3 (PS (2600)-b-PEO(2000))) were produced as described in Example 2.

In Vitro Ammonia Uptake. The in vitro ammonia uptake was studied by means of side-by-side diffusion cells as described in Example 5 with a potassium concentration of 250 mM (final pH 6.8 and osmolality 700 mOsmol/kg).

Figure 11:
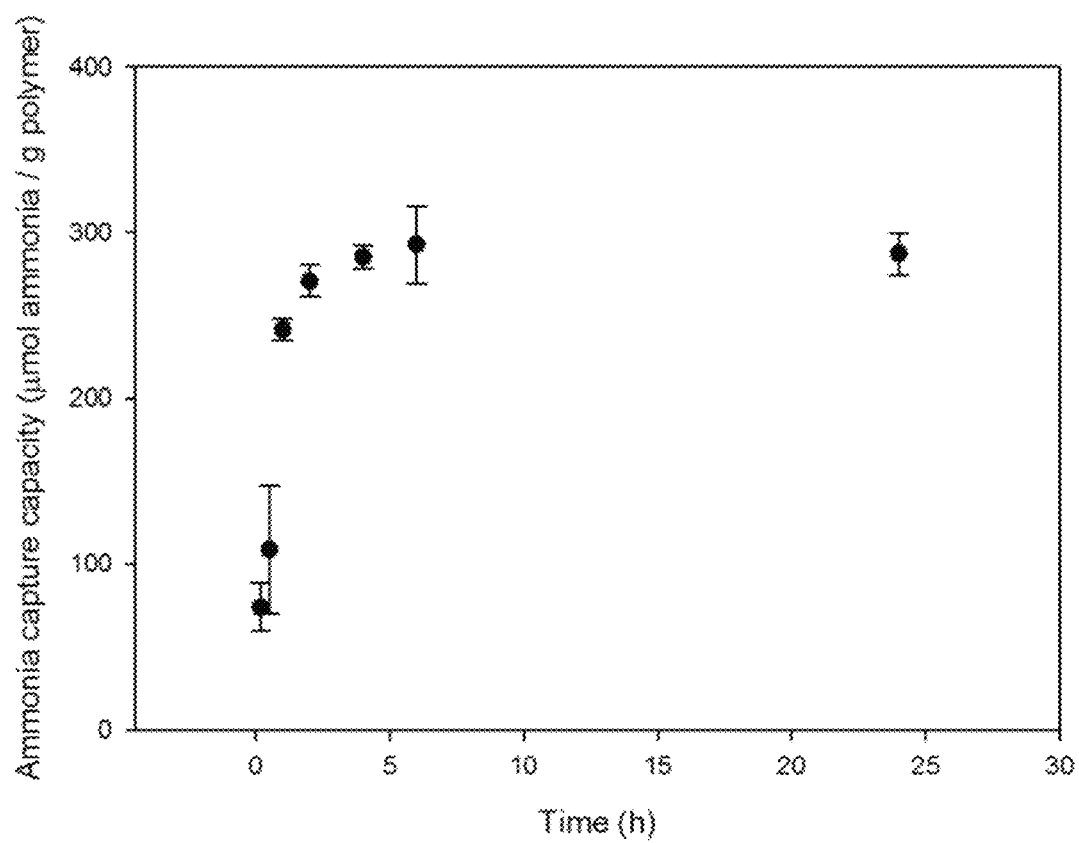
FIG. 11 is a graph showing the in vitro ammonia uptake at high potassium concentrations of transmembrane pH-gradient PS-b-PEO polymersomes with a PS/PEO number average Mw ratio of approximately 1.3 prepared by mixing the polymer-containing organic solvent phase with the aqueous acidic phase using dichloromethane as organic solvent (n=3, mean and standard deviation).

The PS PEO polymersomes were capable of capturing ammonia in bile salt-containing medium at a potassium concentration of 250 mM (n=3). Results are presented in FIG. 11. Each point in the graph represents the average of the group n=3 and the error bars represent the standard deviation.

Example 12: In Vitro Ammonia Uptake of PS-b-PEO Polymersomes with a PS/PEO Number Average Mw Ratio of Approximately 1.3 Prepared by Mixing the Polymer-Containing Organic Solvent Phase with the Aqueous Acidic Phase Using Dichloromethane as Organic Solvent and with Varying Concentrations of Acid Polymersome Preparation. PS-b-PEO polymersomes (PS/PEO number average Mw ratio of approximately 1.3 (PS (2600)-b-PEO(2000))) were produced as described in Example 2 using citric acid solution 100 mM (115 mOsmol/kg), 200 mM (230 mOsmol/kg), 250 mM (300 mOsmol/kg), 300 mM (340 mOsmol/kg), 400 mM (460 mOsmol/kg), 500 mM (580 mOsmol/kg) or 600 mM (700 mOsmol/kg) at pH 2.0.

In Vitro Ammonia Uptake. The in vitro ammonia uptake was studied by means of side-by-side diffusion cells as described in Example 3 (i.e. phosphate buffer only) at pH 6.8 (final osmolality: 300-400 mOsmol/kg).

The PS PEO polymersomes were capable of capturing ammonia in bile salt-free medium (n=3-4). Results are presented in FIG. 12. Each point in the graph represents the average of the group n=3-4 and the error bars represent the standard deviation. The capture capacity of ammonia in transmembrane pH-gradient polymersomes (captured ammonia per gram of polymer) was more than 20-fold higher than that of ammonia-adsorbing microparticles made of AST-120 activated charcoal (captured ammonia per gram of charcoal, Bosoi et al. supra). The scope of the claims should not be limited by the preferred embodiments set forth in the examples, but should be given the broadest interpretation consistent with the description as a whole.

Example 13: In Vitro TMA Uptake at High Bile Salt Concentrations and after Pre-Exposition to an O/W Emulsion of PS-b-PEO Polymersomes with PS/PEO Number Average Mw Ratios Between Approximately 1.4 and 2.0 Prepared by Mixing the Polymer-Containing Organic Solvent Phase with the Aqueous Acidic Phase Using Dichloromethane as Organic Solvent Polymersome Preparation. Poly(styrene)-b-poly(ethylene oxide) (PS/PEO number average molecular weight (Mw) ratios approx. 1.4 (PS(2770)-b-PEO(2000)) and approx. 2.0 (PS(3900)-b-PEO(2000))) were produced as described in Example 2.

In Vitro TMA Uptake. The transmembrane pH-gradient was generated in side-by-side diffusion cells maintained at 37° C. by dilution in phosphate buffer 50 mM under adjustment to pH 6.8 and 300 mOsmol/L in the presence (PS/PEO number average Mw ratios approx. 1.4 and 2.0) or the absence (PS/PEO number average Mw ratio approx. 1.4) of the bile salts sodium cholate (SC), sodium deoxycholate (SDC), and sodium taurocholate (STC) each at 30 mM. In the experiment involving a pre-exposition of the polymersomes to an O/W emulsion (to mimic incorporation in a cream or lotion), 10% (v/v) O/W emulsion (5% (m/v) polysorbate 80, 15% (v/v) mineral oil, and phosphate-buffered saline sufficient to reach the total volume) were added to the polymersome dispersion (PS/PEO number average Mw ratio approx. 1.4) immediately prior to the uptake experiment.

The dual-chamber system was separated by a polycarbonate membrane (pore size=50 nm), physically isolating the polymersomes on one side. The polymer and the TMA concentrations within the diffusion cells were 1.75 mg/mL and 1.5 mM, respectively. At the allotted time, aliquots of 40 µL were taken from the polymersome-free compartment and the TMA concentration was determined by the PocketChem™ BA PA-4140 (Arkray Inc.) which was calibrated with TMA standards. The TMA capture capacity was quantified using equation 3 in which the total TMA concentration refers to the TMA amount in the cells at 10 minutes of incubation:

$$TMA \text{ capture capacity} = \frac{\text{Encapsulated } TMA \text{ } [\mu mol]}{\text{Total polymer mass } [g]} = \frac{\text{Total } TMA \text{ } [\mu mol] - \text{Free } TMA \text{ } [\mu mol]}{\text{Total polymer mass } [g]} \quad \text{Eq. 3}$$

Figure 13:
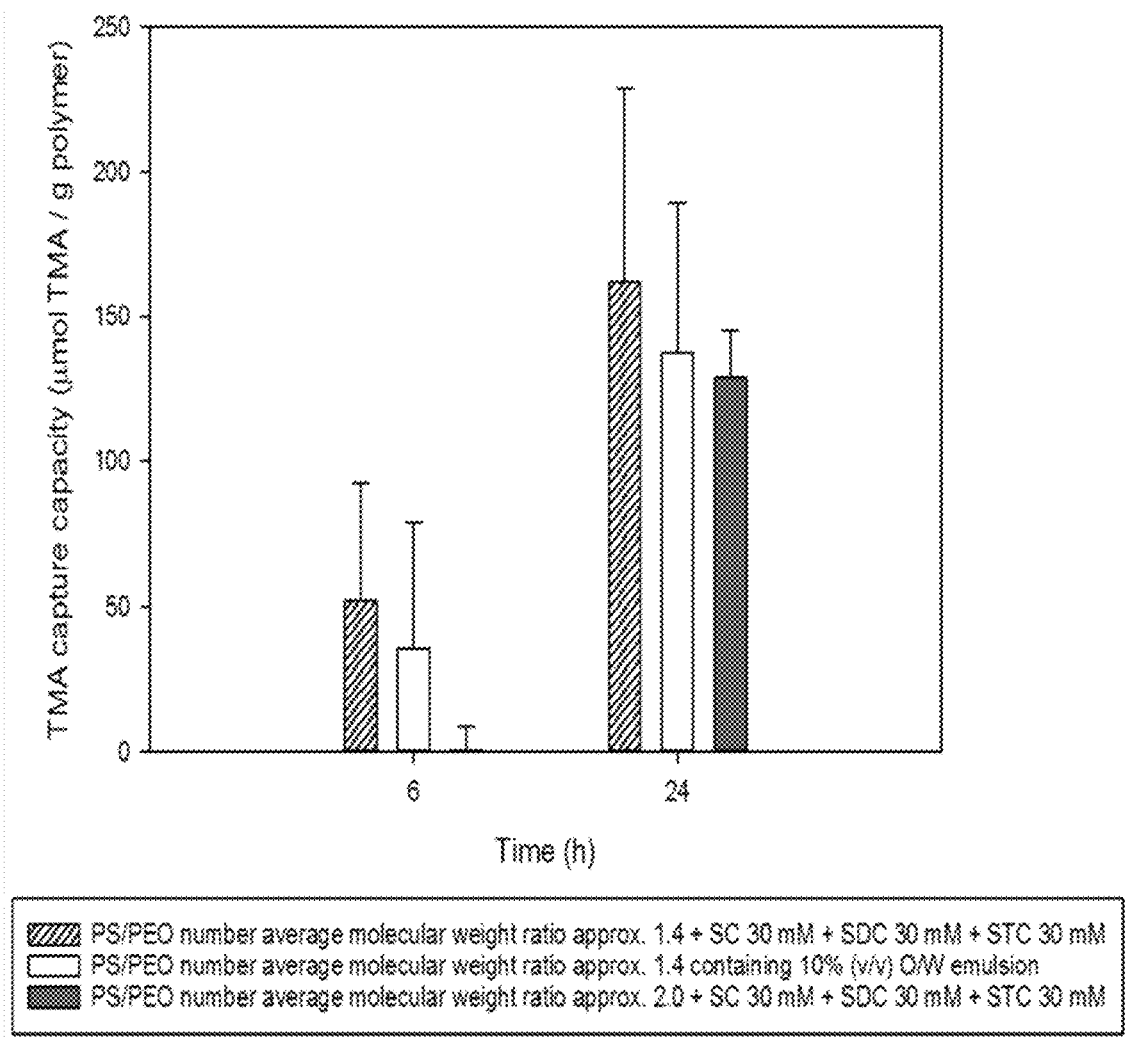
FIG. 13 is a graph showing the in vitro TMA uptake at high bile salts concentrations and after pre-exposition in an O/W emulsion of transmembrane pH-gradient PS-b-PEO polymersomes with a PS/PEO number average Mw ratio of approximately 1.4 or 2.0 prepared by mixing the polymer-containing organic solvent phase with the aqueous acidic phase using dichloromethane as organic solvent (n=3, mean and standard deviation).

The PS PEO polymersomes were capable of capturing TMA in bile salt-containing medium and in an O/W emulsion (n=3). The data show that the polymersomes efficiently captured TMA under harsh conditions mimicking the intestinal tract environment or after incorporation into an O/W emulsion (e.g., lotion or cream, for topical administration). Results are presented in FIG. 13. Each histogram bar in the graph represents the average of the group (n=3) and the error bars represent the standard deviation.

REFERENCES

Bajaj et al. J. Hepatol 2013; 58:S84.
Blankenstein T et al. (2015). Point-of-care (POC) diagnosis of bacterial vaginosis (BV) using VGTest™ ion mobility spectrometry (IMS) in a routine ambulatory care gynecology clinic. Archives of gynecology and obstetrics 292(2), 355-362.
Bosoi et al. Hepatology 2011; 53:1995-2002.
Cashman J R et al. (1999) In-vitro and in-vivo studies inhibition of human flavin-containing monooxygenase form 3 (FMO3) in the presence of dietary indoles. Biochem Pharmacol 58, 1047-1055.
Cashman J R et al. (2003). Biochemical and clinical aspects of the human flavin-containing monooxygenase form 3 (FMO3) related to trimethylaminuria. Current drug metabolism, 4(2), 151-170.
Danks D M et al. (1976) Trimethylaminuria: diet does not always control the fishy odor. The New England Journal of Medicine, 295(17), 962-962
Davankov and Tsyurupa Reactive Polymers 1990; 13:27-42.
Leevy et al. Dig Dis Sci 2007; 52:737-41.
Levy J (2000). The effects of antibiotic use on gastrointestinal function. The American Journal of Gastroenterology, 95(1), S8-S10).
Matoori and Leroux ADDR 2015; 90:55-68.
Mullen et al. Clin Gastroenterol Hepatol 2014; 12:1390-1397.e2.
Neff et al. Clinicoecon Outcomes Res. 2013; 5: 143-152
Neuvonen and Elonen Eur J Clin Pharmacol 1980; 17:51-57.
Neuvonen and Olkkola Med Toxicol 1988; 3:33-58.
Poordad Alim Pharmacol Therap 2006; 25:3-9.
Rose Clinical Pharmacology & Therapeutics 2012; 92:321-331.
Schulman et al. Am J Kidney Dis 2006; 47:565-577.
Stepanova et al. Clin Gastroenterol Hepatol 2012; 10:1034-1041.e1.
Szoka and Papahadjopoulos. PNAS 1978; 75:4194-4198.
Tang W W et al. (2013). Intestinal microbial metabolism of phosphatidylcholine and cardiovascular risk. New England Journal of Medicine 368(17), 1575-1584.
Tang W W et al. (2015). Gut microbiota-dependent trimethylamine N-oxide (TMAO) pathway contributes to both development of renal insufficiency and mortality risk in chronic kidney disease. Circulation research 116(3), 448-455).
Todd W A (1979). Psychosocial problems as the major complication of an adolescent with trimethylaminuria. The Journal of pediatrics, 94(6), 936-937.
Treacy E et al. (1995). Trimethylaminuria, fish odour syndrome: a new method of detection and response to treatment with metronidazole. Journal of inherited metabolic disease, 18(3), 306-312.
Vilstrup et al. Hepatology 2014; 60:715-735.
Yamazaki H et al. (2004). Effects of the dietary supplements, activated charcoal and copper chlorophyllin, on urinary excretion of trimethylamine in Japanese trimethylaminuria patients. Life sciences, 74(22), 2739-2747.
Yeung C K et al. (2007). Functional characterization of genetic variants of human FMO3 associated with trimethylaminuria. Archives of biochemistry and biophysics, 464(2), 251-259
Wang Z et al. (2011). Gut flora metabolism of phosphatidylcholine promotes cardiovascular disease. Nature 472 (7341), 57-63.
Wang Z et al. (2015). Non-lethal inhibition of gut microbial trimethylamine production for the treatment of atherosclerosis. Cell 163(7), 1585-1595.
Wilcken B (1993). Acid soaps in the fish odour syndrome. BMJ: British Medical Journal, 307(6917), 1497.
Wise P M et al. (2011). Individuals reporting idiopathic malodor production: demographics and incidence of trimethylaminuria. The American journal of medicine 124 (11), 1058-1063.

The invention claimed is:

1. A polymersome comprising (a) a membrane, which comprises a dibiock copolymer of poly(styrene) (PS) and poly(ethylene oxide) (PEO), wherein the PS/PEO molecular weight ratio is from 1.3 to 3.8; and (b) a core which encloses an acid.

2. The polymersome of claim 1, wherein the acid is in a concentration that produces a pH between 1 and 6, or between 2 and 5, or between 2 and 4, when the polymersome is hydrated.

3. The polymersome of claim 1, wherein the acid is within an aqueous acidic solution.

4. The polymersome of claim 3, wherein the pH within the aqueous acidic solution is between 1 and 6, or between 2 and 5, or between 2 and 4.

5. The polymersome of claim 1, wherein the acid is a hydroxy acid.

6. The polymersome of claim 1, prepared by a method comprising mixing an organic solvent containing the diblock copolymer with an aqueous phase containing the acid.

7. The polymersome of claim 6, wherein the organic solvent is water immiscible or partially water miscible.

8. The polymersome of claim 1, the core of which further encloses ammonia or its methylated analog after administration of the polymersome to a subject in need thereof.

9. A composition comprising the polymersome defined in claim 1, and at least one pharmaceutically acceptable excipient.

10. The composition of claim 9, wherein the composition is in liquid, semi solid or solid form.

11. A method of making the polymersome defined in claim 1, comprising:
   a. dissolving the diblock copolymer of PS and PEO in an organic solvent, to form a diblock copolymer-containing organic phase;
   b. mixing the diblock copolymer-containing organic solvent phase with an aqueous phase containing the acid so as to form the polymersome; and
   c. removing the organic solvent, wherein the organic solvent is optionally water immiscible or partially water miscible.

12. The method of claim 11, wherein the aqueous phase comprises between 50 and 700 mM of acid.

13. The polymersome of claim 1, wherein the acid is a citric acid.

14. The polymersome of claim , wherein the PS/PEO molecular weight ratio is 1.3 or higher and lower than 3.1.

15. The polymersome of claim 1, wherein the PS/PEO molecular weight ratio is from 1.3 to 2.5.

16. A method treating an ammonia or ammonia methylated analog-associated disease or disorder, or a symptom thereof, comprising a step of administering to a subject in need thereof, a composition comprising a polymersome comprising:
   (a) a membrane, which comprises a diblock copolymer of poly(styrene) (PS) and poly(ethylene oxide) (PEO), wherein the PS/PEO molecular weight ratio is from 1.3 to 3.8, and
   (b) a core which encloses an acid, wherein the composition optionally includes at least one pharmaceutically acceptable excipient.

17. The method of claim 12, wherein the ammonia or ammonia methylated analog-associated disease or disorder is hyperanirnonemia or trimethylaminuria.

18. The method of claim 16, where the administrating step is performed enterally.

19. The method of claim 16, where the administrating step is performed topically.

* * * * *